United States Patent [19]
Beug et al.

[11] Patent Number: 5,905,041
[45] Date of Patent: May 18, 1999

[54] PROCESS FOR PREPARING AND CULTIVATING HEMATOPOIETIC PROGENITOR CELLS

[75] Inventors: Hartmut Beug; Oliver Wessely; Peter Steinlein; Eva Deiner; Maartje Marie von Lindern, all of Vienna, Austria

[73] Assignee: Boehringer Ingelheim International GmbH, Ingelheim am Rhein, Germany

[21] Appl. No.: 08/604,990

[22] PCT Filed: Jun. 28, 1995

[86] PCT No.: PCT/EP95/02516

§ 371 Date: Apr. 29, 1996

§ 102(e) Date: Apr. 29, 1996

[87] PCT Pub. No.: WO96/00777

PCT Pub. Date: Jan. 11, 1996

[30] Foreign Application Priority Data

Jun. 30, 1994 [DE] Germany ............................ 44 22 667

[51] Int. Cl.⁶ ...................................................... C12N 5/00
[52] U.S. Cl. ........................ 435/372; 435/355; 435/375; 435/377
[58] Field of Search ................................ 435/240.2, 7.9, 435/240.22, 240.21, 240.3, 372, 355, 375, 377; 424/9.1, 93.1

[56] References Cited

U.S. PATENT DOCUMENTS 5,270,458 12/1993 Lemischka ............................. 536/23.5
5,405,772 4/1995 Ponting ................................ 435/240.31
5,670,351 9/1997 Emerson et al. ...................... 435/172.3

FOREIGN PATENT DOCUMENTS

WO 93/18136 9/1993 WIPO .
WO 93/25216 12/1993 WIPO .
WO 94/08039 4/1994 WIPO .

OTHER PUBLICATIONS

Hayman, M.J., et al., "Self–Renewal and Differentiation of Normal Avian Erythroid Progenitor Cells: Regulatory Roles of the TGFα/c–ErbB and SCF/c–Kit Receptors," *Cell* 74(*1*):157–169 (Jul. 16, 1993).

Schroeder, C., et al., "The Estrogen Receptor Cooperates with the TFGα Receptor (c–erbB) in Regulation of Chicken Erythroid Progenitor Self–Renewal," *EMBO J.* 12(*3*):951–960 (Mar. 1993).

A copy of the International Search Report for the corresponding PCT Application, WIPO Publication No. WO 96/00777 (International Application No. PCT/EP95/02516).

*Primary Examiner*—Jasemine C. Chambers
*Assistant Examiner*—Karen M. Hauda
*Attorney, Agent, or Firm*—Sterne, Kessler, Goldstein & Fox P.L.L.C.

[57] ABSTRACT

Process for the in vitro production of non-immortalised haematopoietic progenitor cells of the erythroid lineage, in which a population of erythroid progenitor cells is exposed to a combination of growth factors containing a glucocorticoid and an oestrogen and at least one ligand of a tyrosine kinase receptor at least until the cells begin to renew themselves.

17 Claims, 23 Drawing Sheets

PROCESS FOR PREPARING AND CULTIVATING HEMATOPOIETIC PROGENITOR CELLS

FIELD OF THE INVENTION

The present invention relates to a) process for the preparation and in vitro cultivation of haematopoietic progenitor cells, particularly of the erythroidal series.

DESCRIPTION OF RELATED ART

During normal haematopoiesis, pluripotent stem cells develop into progenitor cells which are intended for a specific developmental series (these progenitors are referred to as "committed"); these cells are thought to differ from the pluripotent stem cells in two respects: firstly, they are restricted in their ability to differentiate into a single developmental series or a small number of specific developmental series. Secondly, these committed progenitor cells are generally thought to be either incapable of replicating continuously without simultaneous differentiation (this property is also referred to as the capacity for self renewal) or they do so only transiently (Till and McCulloch, 1980). It is therefore assumed that the progenitor cells, committed to a specific developmental series, begin a predetermined programme of changes in gene expression which ends with the formation of a terminally differentiated cell. Pluripotent stem cells, on the other hand, are thought to retain their capacity to undergo numerous cell divisions without changing their state of differentiation or gene expression. The programme which the progenitor cells undergo is obviously compatible with undergoing numerous cell divisions, but it is assumed that during each division the cells will undergo changes, however slight, in their state of differentiation or gene expression (Keller, 1992).

This view that a fixed determination/differentiation programme determines the development of the committed progenitor cells has recently been called into question in various ways: firstly, some observations lead one to assume that normal committed progenitors can undergo extended phases of expansion, indicating self-renewal or related processes. Murine B-lymphocyte progenitors renew themselves constantly under a series of culture conditions (stromal feed cell layers plus interleukin 7), but differentiate under other conditions into mature B-cells (Rolink et al., 1991). Similarly, individual murine granulocyte macrophage colony forming cells (GM-CFC), depending on the concentration of GM-CSF, may produce between 100 and more than 10,000 mature granulocytes and macrophages (Metcalf, 1980).

Another phenomenon which is difficult to reconcile with a fixed programme of the development of committed progenitors consists of leukaemias. Although in some cases these start from pluripotent stem cells, other leukaemias clearly derive from committed progenitors (Sawyers et al., 1991). Regarding the latter type there is a frequently expressed concept that the genetic changes which occur in leukaemia cells give them the abnormal ability of self-renewal, a quality which the corresponding normal progenitor cell does not have. Whereas in the chronic phase of chronic myeloid leukaemia (CML) clones of altered, multipotent progenitor cells overgrow the corresponding normal clones (possibly on account of their greater capacity for self-renewal) other mutations which take place during the blast crisis lead to a massive outgrowth of immature progenitors and maturing cells of a special development series, which is interpreted as self-renewal of abnormal committed progenitors (Daley et al., 1990; Elefanty et al., 1990; Kelliher et al., 1990).

Recently, it was shown, in chicken cells, that normal haematopoietic progenitors which are committed to the erythroid developmental series are capable under certain conditions of sustained self-renewal (Schroeder et al., 1993; Hayman et al., 1993). It was shown that the combined effect of TGFα (Transforming Growth Factor, a ligand for the chicken homologue of epidermal growth factor receptorlc-erbB-protooncogene (TGFαR/c-erbB; Lax et al., 1988) and oestradiol induced the outgrowth of normal progenitors from chicken bone marrow. These cells are known as SCF/TGFα-progenitor cells on account of their ability to grow out from cultures which contain TGFα plus oestradiol or SCF (stem cell factor) (cells which grow in the presence of SCF are termed SCF progenitor cells). SCF/TGFα-progenitor cells express the c-kit-protooncogene, the oestradiol receptor and TGFαR/c-erbB and are capable of sustained self-renewal in the presence of TGFα plus oestradiol until the end of their normal in vitro life. It has also been shown that erythroid progenitors which cannot be distinguished from normal CFU-Es (colony-forming unit erythroids) in terms of all the properties investigated (known as SCF-progenitors) could be cultivated from bone marrow using chicken-SCF (Hayman et al., 1993). By contrast to the SCF/TGFα progenitors with the capacity for self-renewal, the SCF progenitors lacked the expression of TGFαR/c-erbB, and in the presence of SCF the cells exhibited only transient self-renewal during the period of 7 to 10 days. When they were switched to differentiation factors (erythropoietin plus insulin), both types differentiated with indistinguishable kinetics in erythrocytes. This indicated that the SCF/TGFα-progenitors are not the progenitors of SCF progenitors as was originally assumed on account of the fact that SCF/TGFα-progenitors are relatively rare (1 in 15,000 normal bone marrow cells), whereas the SCF-progenitors are much more common (1 in 300–500; Hayman et al., 1993). However, these results failed to answer the question as to whether the self-renewing SCF/TGFα-progenitors derived from even more immature progenitors. One possible answer is that these cells constitute a separate, rare cell type which occurs in the bone marrow and develops from multipotent progenitors like a separate cell line. One alternative answer would be that these cells derive from normal CFU-Es which acquire the potential for self-renewal only under the effect of specific combinations of growth factors and hormones which are not normally active in erythropoiesis.

In earlier studies (Schroeder et al., 1993) it was shown that there are two fundamental requirements for the outgrowth of SCF/TGFα-progenitors from bone marrow: firstly, a specific length of time—the outgrowth never occurred until 11 to 14 days had passed; secondly, the dependency on both TGFα and oestradiol, which was demonstrated by the fact that the outgrowth of the cells was completely inhibited by an oestradiol antagonist and did not occur in the absence of TGFα. If the first answer is correct and SCF/TGFα-progenitors are a particular cell type which is always present in normal bone marrow and is dependent only on TGFα and oestradiol, other factors should not have any significant effect on the frequency of these cells; however, two observations would tend to speak against this simplified model: firstly, it has been found that the outgrowth of SCF/TGFα-progenitors was strongly inhibited in the presence of chicken serum which had been treated with animal charcoal, whereas in Freon-treated or untreated serum it was not substantially affected. This leads one to assume that in addition to TGFα and oestradiol, other factors which are eliminated by the animal charcoal treatment have an effect on the SCF/TGFα-progenitors at some stage of their formation. It has also been observed that bone marrow cells kept in SCF plus oestradiol were stationary after 8 to 10 days but started to grow slowly again on approximately the 14th day. These cells expressed TGFαR/c-erbB in a relatively high concentration (Hayman et al., 1993) and could be grown in TGFα plus oestradiol, which leads one to suppose that these cells are SCF/TGFα-progenitors which had grown out of the original population of SCF-progenitors.

SUMMARY OF THE INVENTION

The aim of the present invention is to clarify the mechanisms which are involved in the formation of haematopoietic progenitors of the erythroid lineage, which express c-Kit and TGFαR/c-ErbB (referred to within the scope of the present invention as "SCF/TGFα-progenitors"), and on the basis of the knowledge obtained, to prepare a process for cultivating normal erythroid progenitor cells in vitro.

In particular, the intention is to provide a process which makes it possible to mass produce non-immortalised and hence genetically unaltered human haematopoietic progenitor cells.

DESCRIPTION OF THE PREFERRED EMBODIMENTS

Within the scope of the present invention it was first shown, regarding chicken cells, that in the presence of SCF, TGFα, oestradiol and specific unidentified chicken serum factors SCF/TGFα-progenitors develop in cultures of purified SCF-progenitors.

It has been shown that when SCF-progenitors are cultivated in the presence of a combination of SCF, TGFα, oestradiol and initially undefined factors from normal or anaemic chicken serum, a large proportion of these cells undergo neither differentiation nor apoptosis, but begin to express increasing quantities of TGFαR/c-erbB in a strictly time-dependent pattern, resulting in the production of SCF/TGFα-progenitors after 10 to 14 days. At this time, the expression of TGFαR/c-erbB in the cells is obviously high enough to allow proliferation-in the presence of TGFα and oestradiol in the absence of SCF. When specially treated chicken sera were used it was shown that no SCF/TGFα-progenitors are formed if one of these three factors (SCF, TGFα or oestradiol) was missing. On the other hand, the formation of the proliferating progenitors in the presence of SCF, TGFα and oestradiol was partly inhibited, although not eliminated, if the unidentified activity of the chicken serum was absent. Further tests on a chicken model showed that the initially unidentified activity can be at least partly replaced by two defined factors: 1. the glucocorticoid-receptor-ligand dexamethasone and 2. the tyrosinekinase receptor-ligand insulin-like growth factor 1 (IGF-1). It could also be assumed that erythropoietin is another factor which is responsible for the activity in the chicken serum.

When SCF-progenitors were cultivated in SCF, TGFα and oestradiol, SCF/TGFα-progenitors became concentrated in the culture, until after about two to two and a half weeks they were predominant in the culture. The expression of TGFαR/c-erbB increased with time when the SCF-progenitors were cultivated in SCF, TGFα and oestradiol. On the basis of the mass culture experiments carried out, it was initially impossible to distinguish between two possible ways in which the SCF/TGFα-progenitors had formed from the cultures of SCF-progenitors. The first (trivial) possibility would be that a small number of SCF/TGFα-progenitors which express c-erbB exist in normal bone marrow and hence in SCF-progenitor populations from the outset, these cells gradually overgrowing the SCF-progenitors (if the culture is carried out in the presence of SCF, TGFα and oestradiol, which might possibly help to give these cells a growth advantage). The more interesting, untrivial possibility, however, is that the bone marrow does not contain, at the outset, any erythroid progenitors capable of proliferating in TGFα and oestradiol alone, but that SCF/TGFα-progenitors are induced to develop from SCF-progenitors if all three factors plus certain chicken serum components or dexamethasone and IGF-1 (see above) are present.

The experiments carried out within the scope of the present invention showed that this latter hypothesis is correct, i.e. that SCF/TGFα-progenitors can develop from SCF-progenitors. The results obtained with chicken cells showed that normal erythyroid progenitors (SCF-progenitors which resemble the colony forming unit erythroid (CFU-E) progenitor in all the qualities investigated) develop under the control-of at least two growth factors (SCF, TGFα) plus a steroid hormone (oestradiol) and an initially undefined activity from chicken serum, which was later partially identified as dexamethasone plus IGF-1, into another type of erythroid progenitor (SCF/TGFα-progenitor). This other type of progenitor is characterised by its newly acquired expression of TGFαR/c-erbB (which corresponds to the mammalian EGF/TGFα receptor) and its ability to undergo sustained self-renewal as a reaction to TGFα and oestradiol. The differentiation programme of the SCF/TGFα-progenitors after treatment with differentiation factors (EPO, insulin) strongly resembles the normal CFU-E-progenitor (Hayman et al., 1993).

Since it has hitherto been assumed that erythroid progenitors are irreversibly committed to differentiation and undergo a fixed programme of 5 to 10 cell divisions, the finding obtained with chicken cells that they may acquire a self-renewal potential under certain conditions by changing their differentiation programme ("developmental switch") was of considerable interest, provided that these findings were valid for mammalian or even human cells. Within the scope of the present invention it is shown that the results of the chicken system are applicable to human cells to a surprising degree.

There is a need for human haematopoietic progenitor cells which can be cultivated in vitro particularly for the purposes of transplanting such cells in the treatment of cancer and AIDS patients. A further use of such transplantation is the treatment, by gene therapy, of chronic anaemias in which the maturing of the erythrocytes is disrupted, e.g. thalassaemia and other genetically caused anaemias.

One of the few definite preconditions required for successful transplantation of blood cells is the expression of CD34. However, it is not known at which stage of development the subpopulation of the $CD34^+$-cells is at, which is actually responsible for successful transplantation, although it is assumed that the developmental series and stage of differentiation of the cells play a part.

Autologous or allogenic transplantation of haematopoietic progenitor cells involves difficulties, one of the main problems being that a sufficient number of cells having the proliferation potential necessary for successful reconstitution of the haematopoietic system has to be transplanted and the criteria which determine this potential have not been adequately researched as yet.

Hitherto, for allogenic transplantations, bone marrow cells from healthy donors are frequently used; for autologous transplants, stem cells from peripheral blood are used which are mobilised during the recovery of the patient from chemotherapy and/or by treatment with recombinant growth factors. These methods are expensive; in addition, they involve considerable unpleasantness for the donor or yield poor results owing to haematological changes in the patient. It has therefore recently been proposed as an alternative that stem cells be used from cytokine-treated healthy donors.

Another alternative regarded as highly promising is to use umbilical cord blood cells instead of bone marrow or $CD34^+$-positive cells from peripheral blood, as the majority of haematopoietic stem and progenitor cells from umbilical cord blood are at an earlier stage of development and have a greater proliferation potential. However, since about 1.5 litres of umbilical cord blood would be necessary for transplanting in an adult, the requirement being $5 \times 10^5 - 2 \times 10^6$ $CD34^+$-cells per kg of body weight, this method is subject to limits in the treatment of adults.

There is therefore a need for a process which permits mass culture of autologously or allogenically transplantable haematopoietic progenitor cells.

Within the scope of the present invention it has been shown that human erythroid progenitor cells, surprisingly, exhibit similar behaviour to the corresponding chicken cells, in that they undergo a change in their differentiation programme as a result of which they acquire a potential for self-renewal. Like the chicken cells, the cells required SCF, oestradiol and dexamethasone in order to acquire the ability for sustained self-renewal. IGF-1 had a positive influence on the growth of chicken and human erythroblasts. Some of the cells in the culture of human erythroid progenitors, which was obtained within the scope of the experiments carried out, reacted to ligands of the EGF-receptor, which is an additional indication that the human cells are similar in their behaviour to the chicken SCF/TGFα-progenitors under the influence of certain growth and differentiation factors.

The present invention is thus also based on the critical realisation that a change in the differentiation programme of human erythroid precursors must take place, on the basis of which change they acquire the ability for sustained outgrowth. This change in the differentiation programme should be induced by the interaction of factors which are ligands of representatives of the same receptor groups the activation of which induces the development of self-renewing erythroid progenitors from chicken bone marrow.

The invention thus relates to a process for in vitro production of non-immortalised haematopoietic progenitor cells of the erythroid lineage, which is characterised in that cells containing a population of erythroid progenitors, in a medium which contains the usual components necessary for the growth of erythroid cells, are exposed to a combination of growth factors, containing at least one ligand of the oestrogen receptor and at least one ligand of the glucocorticoid receptor and at least one, preferably at least two ligands of a tyrosine-kinase receptor, at least until the cells begin to renew themselves, and subsequently, if desired, the cells are further cultured in a medium which contains the factors required for sustained self-renewal.

By treating the cells with the combination of growth factors (hereinafter referred to as "factor combination") the cells undergo a change in the differentiation programme. This is accompanied by a change in the expression pattern of the receptors which are newly expressed or highly regulated by the action of the factor combination, and/or by changing the expression pattern of protein components of the cell signal transmission pathways triggered by these epigenetic changes.

The term "self renewal" refers to the ability of cells to form daughter cells which do not mature measurably during the subsequent cell divisions, i.e. in which there is no measurable further accumulation of those proteins which are typical of the mature cells but may also be expressed in small amounts in progenitor cells. Another important criterion for self-renewal is that the ratio of proteins of the mature (terminally differentiated) cell (e.g. haemoglobin) and proteins which are necessary for the function of each cell (so-called "housekeeping proteins", e.g. glycolytic enzymes) does not measurably change.

Preferably, the process according to the invention is applied to human cells.

The starting cell material used is preferably a cell population of bone marrow, peripheral blood or, in a particularly preferred embodiment, umbilical cord blood containing a concentration of CD34-positive cells. Concentration may be achieved by methods known from the literature; a survey of such methods is given in the textbook "Hematopoietic Stem Cells, The Mulhouse Manual", 1994.

The cells are cultivated in vitro at least until self-renewal occurs. Purely externally, cells with potential for self-renewal can be recognised by the fact that they are continuously dividing in the culture, i.e. proliferating exponentially, for a period of time corresponding to the in vitro life of the cells (50–70 generations in the case of human cells) or part of this life, and they have a constant size and a comparatively small content of erythrocyte proteins (e.g. haemoglobin). Anyone skilled in the art can tell from these criteria, in preliminary tests, the point in time in which the cells acquired a potential for self-renewal and can accordingly define the duration of cultivation.

The self-renewal of the human cells of the erythroid lineage which are obtainable within the scope of the present invention is characterised in that the cells divide without any appreciable differentiation over a substantially longer period of time than has hitherto been shown for normal human BFU-Es (burst forming unit erythroids).

The factor combination is preferably a combination of at least three and preferably at least four factors, at least two of them being ligands of tyrosine kinase receptors. There is a quantity of literature on receptors of this type, the families and sub-families to which they belong, their ligands and the signal transmission pathways triggered by their activation and new examples are constantly being identified. What is common to the tyrosine kinase receptors is the fact that after the binding of their ligand they themselves phosphorylate to tyrosines. After this autophosphorylation the phosphotyrosine groups interact with specific cytoplasmatic molecules, thereby triggering the cell response to the growth factors.

The family of the tyrosine kinase receptors is divided into various classes and sub-families; these include the class to which the EGFR family, HER2/neu/c-erbB-2 and HER3/c-erbB-3 belong; the class to which the insulin receptor, the insulin related receptor and the IGF-1 receptor belong; the class which comprises PDGF receptor, PDGFβ receptor, MCSF-1 receptor and c-kit; the class of the fibroblast growth factor receptors (FGF-receptor1, FGF receptor2, FGF receptor3, FGF receptor4) and the HGFR receptor (hepatocyte growth factor receptor). Some of these classes share the feature that the kinase domain is interrupted by a sequence. Regarding the tyrosine kinase receptors and their ligands, we refer to the summarising article by Fantl et al., 1993 and Van der Geer, 1994, including the literature specifically cited therein regarding the individual receptors.

The factor combination of tyrosine kinase receptor ligands consists of at least one ligand for receptors from various families within the tyrosine kinase receptors. An example of such a combination is i) at least one ligand of a tyrosine kinase receptor which has a continuous kinase domain, and ii) at least one ligand of a tyrosine kinase receptor which has a kinase domain interrupted by an insert.

Examples of representatives of the receptors defined in i) are the members of the EGF-receptor family (Human Epidermal Growth Factor Receptor 1–4); other only partly identified receptors belong to this family.

Ligands of the receptors defined in i) include, inter alia, EGF, TGFα, NDF (Neuronal Differentiation Factor; Peles and Yarden, 1993), including the variants produced by differential splicing, Heregulin, Amphiregulin, Glial Growth Factor etc. (Fantl et al., 1993).

Ligands of the receptors defined in ii) include, inter alia, the c-kit ligand SCF (Stem Cell Factor), Platelet Derived Growth Factor (PDGF) alpha and beta, all the members of the fibroblast growth factor family, CSF-1 (Colony Stimulating Factor 1) and vascularising factors (e.g. VEGF, Vascular Endothelial Growth Factor) (Fantl et al. 1993).

In addition, there are a plurality of tyrosine kinase receptors which cannot be clearly allocated to these two groups (the ligands of which are only partly known), activation of which by the corresponding ligands may cause the outgrowth of human progenitor cells; the corresponding ligands may also be used within the scope of the present invention. These receptors include: Hepatocyte Growth Factor Receptor (the ligand of which is also known as "Scatter factor"; the findings obtained by Galimi et al., 1994 indicate that the Hepatocyte Growth Factor Receptor (HGFR), which is assumed to activate the same signal transmission pathways as the EGF receptor, plays an important part in CD34$^+$ cells and human erythroid progenitor cells produced therefrom), c-sea and c-ros (the ligands of which have not yet been identified), various epithelial cell-specific receptors the ligands of which are unknown, a group of receptors cloned from erythroid cells which have recently been described (e.g. by Tamagnone et al., 1993 and Kaipainen et al., 1993), the ligands of which are also as yet unknown, and also the members of the neurothrophin receptors (trk, trk-B, trk-C with the ligands NGF, BNDF, etc.), and receptors of the insulin receptor family (insulin receptor, IGF-1 receptor etc.).

Without wishing to be tied to the theory, it would appear to be essential, for triggering the change in the differentiation programme, that different signal transmission pathways are set in motion by the binding of the ligands and the consequent activation of the receptors defined in i) and ii).

Apart from the two ligands of the tyrosine kinase receptors, the factor combination contains:

iii) at least one ligand of the oestrogen receptor and at least one ligand of the glycocorticoid receptor.

Within the scope of the present invention, natural or synthetically produced steroid hormones which, like oestradiol, activate the oestrogen receptor or, like hydrocortisone, activate the glycocorticoid receptor, are suitable.

Additionally, the factor combination may possibly contain ligands of the progesterone receptor, such as aldosterol and progesterone.

What is common to these hormones is that a) they are low molecular, b) they bind to receptors located in the nucleus which constitute transcription factors regulated in their activity by the hormone (proteins which alter the genes in their activity) and c) they are capable of changing the differentiation programme of cells in some of the systems investigated hitherto.

Within the scope of the present invention, it has been found that, apart from an oestrogen, dexamethasone, a glucocorticoid, in particular is of crucial importance in the outgrowth of self-renewing chicken and human erythroid progenitor cells.

In addition, the factor combination iv) may contain one or more additional factors.

The additional factors iv) may be in particular ligands which at least speed up the change in the differentiation programme and hence bring about a more efficient outgrowth of the cells. These factors are generally added to the medium right at the beginning of the culture, whilst it should be borne in mind that different factors may be necessary at different times during the change to the differentiation programme. With regard to accelerating the change in the differentiation programme, therefore, it may be advisable to eliminate from the medium any factors which are essential for triggering this process but are later inessential or even disadvantageous, at a suitable point in time which may be determined by a series of tests. Additional factors which may be considered are as follows:

1. Ligands of receptors which act by serine phosphorylation of target proteins. (TGFβ-receptor family). In particular, the ligands activin, inhibin, BMP etc. which play a part in early embryonic development are important (Laufer, 1993; Hogan, 1993).

2. Ligands of other tyrosine kinase receptors, particularly IGF-1 or hepatocyte growth factor (HGF).

3. Representatives of the large group of cytokines or interleukins (growth and differentiation factors in the haematopoietic and immune system). Virtually all these cytokines bind to receptors which do not themselves have any known enzyme activity, but some of the receptors form complexes with intracellular tyrosine kinases. A summary of this constantly growing family of receptors and their ligands is provided in Boulay and Paul, 1993.

An essential feature for the activity of a cytokine which can be used within the scope of the present invention is that first of all it stimulates the proliferation of immature progenitors and secondly does not have any effect which negatively influences cell growth and/or triggers apoptosis (programmed cell death). Within the scope of the present invention, preferred cytokines are IL-1, IL-3, IL-11 and IL-13. EPO is particularly preferred.

The population of cells obtained by the action of the combination of factors may be frozen after the start of self-renewal and thawed as necessary and thereafter either further cultivated or transplanted directly in order to make use of the self-renewal potential of the cells, acquired in vitro, for proliferation in vivo.

However, the cells may be cultivated beyond the length of time during which they acquire the self-renewal potential, so as to obtain a larger number of proliferating cells within the population.

Further cultivation of the proliferating cells is carried out in the presence of those growth and differentiation factors which the cells require for sustained self-renewal.

For chicken cells, TGFα is one of the factors needed for the sustained self-renewal potential and hence for the cultivation of the cells over a fairly long period of time in order to obtain a large number of cells. For human cells, the factors preferably used for further cultivation of the cells are ligands of the type defined in i) such as EGF and/or TGFα, and/or HGF, as well as SCF, and also EPO and IGF-1.

The suitable combination of factors both for the induction of the self-renewal and for further cultivation of the proliferating cells is determined by testing the response of the cells and their growth characteristics under the effect of various mixtures of factors at various times; examples of such tests are described, inter alia, in Examples 4b), 5, 7b and 8. The factor mixture is preferably optimised by first testing various multi-component mixtures so as to identify the most effective mixture. Then, one factor is eliminated step by step from the most effective mixture and the behaviour of the culture with and without the factor is compared. To summarise, the factor combination is adjusted so as to achieve the most rapid and efficient outgrowth possible for self-renewal of viable cells with the fewest possible factors.

The treatment with the combination of SCF, TGFα, oestradiol and another activity, carried out within the scope of the present invention, resulted in an increase in the expression of biologically active TGFαR/c-ErbB in chicken and human cells, which manifested itself in chicken cells by an increase in autophosphorylated receptor after the addition of ligand; the further activity, in the case of chicken cells, was an unidentified activity in the chicken serum and, in the case of human cells, EPO.

In one embodiment of the invention, the factor combination for the preparation of human haematopoietic progenitor cells consists of i) a ligand of a receptor from the family of the EGF receptors and/or the HGF receptor, ii) a ligand of c-Kit;

iii) oestradiol and dexamethasone, and iv) erythropoietin and IGF-1.

In one particular embodiment of the invention i) is EGF and/or TGFα and/or HGF, and ii) is SCF.

If the factors are components of the medium in a sufficient concentration, e.g. as serum components, they must not be added separately.

The usual components contained in the medium apart from the factor combination and necessary for the growth of the cells, such as vitamins, amino acids, etc., are well known to those skilled in the art; they are contained in commercially available media and may be found in the relevant textbooks, such as "Haematopoietic Stem Cells, The Mulhouse Manual", 1994 and specialist articles such as Sawada et al., 1990.

The cells obtained by the process according to the invention may, after removal of the culture medium, be suspended in a medium suitable for therapeutic use, e.g. human serum albumin (HSA) or autologous plasma and used for allogenic or autologous transplantation. The process according to the invention may be used, inter alia, to cultivate haematopoietic cells from a supply of blood cells of an individual whose production of CD34 positive cells has been stimulated, e.g. by treatment with cytokines, in the event of the need for a transplant. These haematopoietic cells can be stored frozen, thawed when needed, amplified by culturing in vitro and used, optionally after suitable gene transfer, for therapeutic purposes in the patient.

An example of a strategy in which genetically altered human erythroid cells cultivated in vitro may be used is the treatment of sickle cell anaemia by gene therapy. This inherited disease occurs particularly in the USA in a large number of coloured patients. One possible procedure consists in cultivating erythroid progenitors from bone marrow, peripheral blood or (in the event of prenatal diagnosis) umbilical cord blood, gene transfer of the globin-gene locus which carries the hereditary persistence of foetal haemoglobin (HPFH) mutation and administration of these genetically altered somatic cells (the germ path is unaffected) to the patient.

Gene transfer into the cells obtained according to the invention may be carried out by standard methods for the transfection of such cells. These methods include gene transfer using viral vector (retrovirus, adenovirus, adeno-associated virus) or using non-viral systems based on receptor-mediated endocytosis; summaries of conventional methods are provided for example by Mitani and Caskey, 1993; Jolly, 1994; Vile and Russel, 1994; Tepper and Mule, 1994; Zatloukal et al., 1993, WO 93/07283.

BRIEF DESCRIPTION OF THE FIGURES

FIGS. 2A, 2A-1, 2B, 2B-1, 2C, 2C-1, 2D, and 2D-1: Expression and bioactivity of c-Kit and c-ErbB during the proliferation of SCF-progenitors in SCF, TGFα and oestradiol FIGS. 3A–3C Change in growth factor dependency of SCF progenitors which proliferate in SCF, TGFα and oestradiol FIGS. 4A, 4A-1, 4B, and 4B-1: Experimental strategy for clarifying the formation of SCF/TGFα progenitors

FIGS. 11A-1, 11A-2, 11B, 11C, and 11D: Characterisation of human erythroid progenitors cultivated in vitro

EXAMPLE 1

Figure 1:
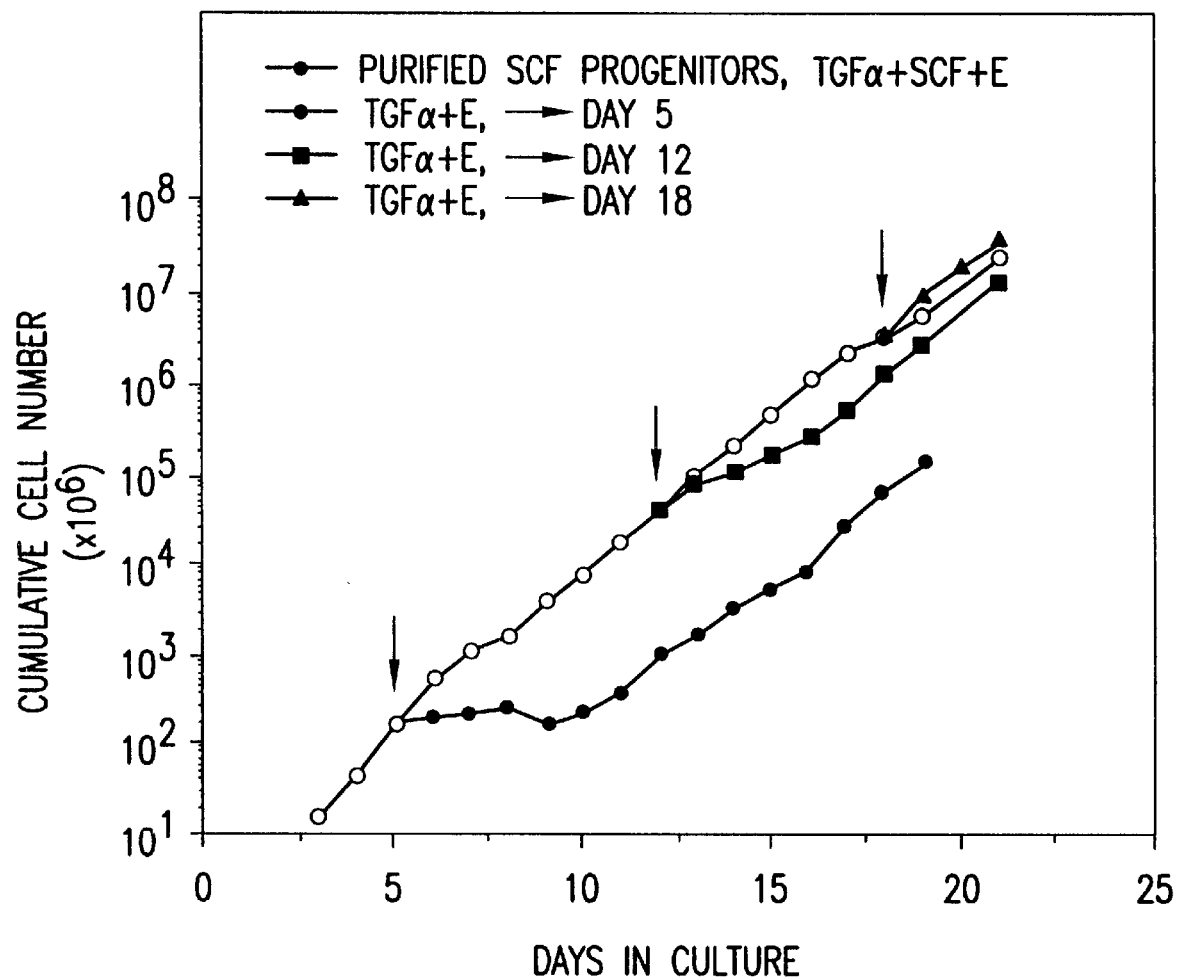
FIG. 1: outgrowth of SCF/TGFα-progenitors from SCF progenitors

Concentration of SCF/TGFα progenitors by cultivating SCF progenitors in SCF, TGFα and oestradiol In order to determine systematically whether SCF progenitors contain SCF/TGFα progenitors or whether they contain cells which can develop into this type of cell, cells from a 6 day old culture of purified SCF progenitors (Hayman et al., 1993) were cultivated in CFU-E medium containing 100 ng/ml of recombinant SCF, 5 ng/ml of TGFα and $5 \times 10^7$M oestradiol and the cell proliferation was monitored by counting using the system described by Hayman et al., 1993 (CASY-1, sharpness system). (The rationale behind using all three factors was to keep the SCF progenitors alive as long as possible and at the same time stimulate the growth of any SCF/TGFα progenitors present or generated in the culture.) The results of this experiment are shown in FIG. 1. Surprisingly (and in sharp contrast to the results obtained in a comparative test by growing the same cells in TGFα plus oestradiol) the cells showed only a weak, transient decrease in their growth rate around day 8 to 10 but continued to proliferate exponentially thereafter, with a doubling time of 18 to 22 hours from day 25 to 30, after which they underwent senescence (FIG. 1, open circles).

In order to determine whether the SCF progenitors which had been cultivated in SCF, TGFα and oestradiol contained SCF/TGFα progenitors or had developed themselves, and to obtain a rough estimate of their numbers, aliquots of the culture were taken at different times, washed, transferred into CFU-E medium containing TGFα and oestradiol but no SCF, and the number of cells was compared with that of the culture which contained all three factors. (The cells were kept at a density of between $1 \times 10^6$ and $2 \times 10^6$ per ml by suitable dilution with fresh medium and the cumulative cell numbers were calculated from the numbers of cells obtained and the corresponding dilution factors (Schroeder et al., 1993;

Hayman et al., 1993)) (FIG. 1, arrows). When the three-factor combination was removed from the cells on day 5, they immediately stopped proliferating. The numbers of cells remained approximately constant up till day 11.

During this time, most of the cells underwent apoptosis (these were not distinguished from the living cells by the cell counter), whilst some healthy clumps remained, which began to form the culture around day 13 to 14. After that, the cells underwent growth, in the presence of TGFα plus oestradiol, which was indistinguishable in its kinetics from that of the control culture (FIG. 1, solid circles).

Different behaviour of the cells was observed when cells which had been cultivated in SCF, TGFα and oestradiol were transferred on day 12 into medium containing TGFα plus oestradiol (FIG. 1, solid rectangles). Up till this time, only some of the cells had suffered apoptosis whilst many others carried on growing, which became apparent as a temporary reduction in the growth rate between days 13 and 16. After that, the cells grew at similar speed in TGFα plus oestradiol to the control cells. After 18 days culture, transfer of all three factors to TGFα plus oestradiol had no noticeable effect on the cell proliferation (FIG. 1, solid triangles), indicating that, at this time, the culture consisted entirely of SCF/TGFα progenitors.

EXAMPLE 2

Increase in the expression of bioactive TGFαR/c-erbB in SCF progenitors cultivated in SCF, TGFα and oestradiol
a) Expression and bioactivity of c-Kit and c-ErbB during the proliferation of SCF progenitors in SCF, TGFα and oestradiol On the basis of the results obtained in Example 1, it was assumed that the SCF progenitors cultivated in SCF, TGFα and oestradiol were either overgrown by SCF/TGFα progenitors which were there from the outset or had developed into such. The purpose of the experiments was to show that the proliferating cells actually express bioactive TGFαR/c-ErbB, which should become apparent in the biochemical reaction (autophosphorylation) or biological reactions (stimulation of proliferation in corresponding assays) to be expected. For this purpose, on days 6, 12 and 20, aliquots of the culture and control culture (see Example 1) were taken, washed, incubated overnight in medium without growth factors, stimulated for 5 minutes with various factor combinations and further treated as described by Hayman et al., 1993 and used for the phosphotyrosine blot and the subsequent Western blot (using anti-TGFαR- or c-erbB-antibodies).

Figures 2A, 2B:
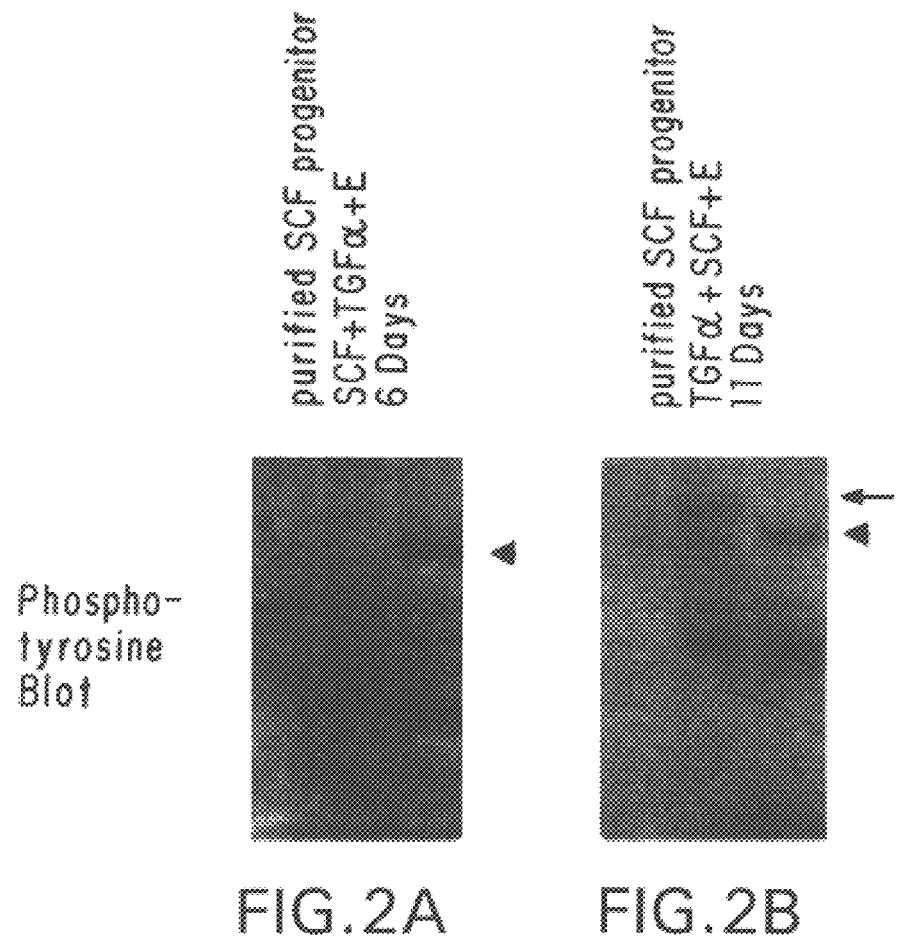
Figures 1, 2A, 2B:
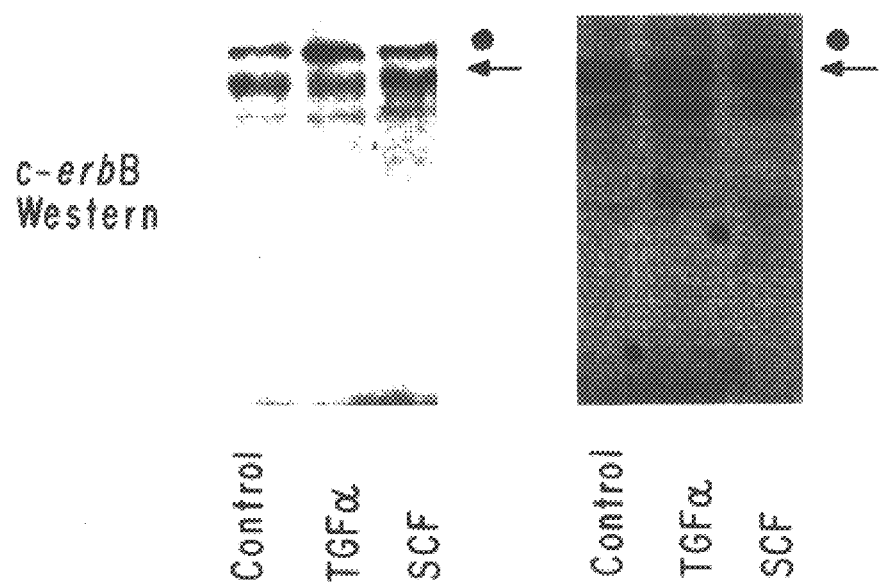

After a total of 6 days (after an initial 3 days in SCF) the cells cultivated in SCF, TGFα and oestradiol showed the clear phosphorylation of c-Kit expected on account of the reaction to SCF and they expressed large quantities of c-Kit. By contrast, according to Western blot analysis, the cells contained only very tiny amounts of TGFαR/c-ErbB and there was no visible autophosphorylation of c-ErbB (these experiments are shown in FIG. 2A, the arrows indicating the 170 kd TGFαR/c-ErbB protein whilst the tips of the arrows indicate the 140 kd SCF-R/c-Kit protein; the black circle in the lower boxes indicates the position of a background band without reference to TGFαR/c-ErbB).

After 11 days, the expression of TGFαR/c-ErbB had increased significantly, as demonstrated by c-ErbB-Western blot. In addition, a weak, although significantly detectable reaction of autophosphorylation of the c-ErbB protein could be made out on the ligands (FIG. 2B-1). As expected, the cells were still expressing autophosphorylated c-Kit (FIG. 2B-1).

Figures 2C, 2D:
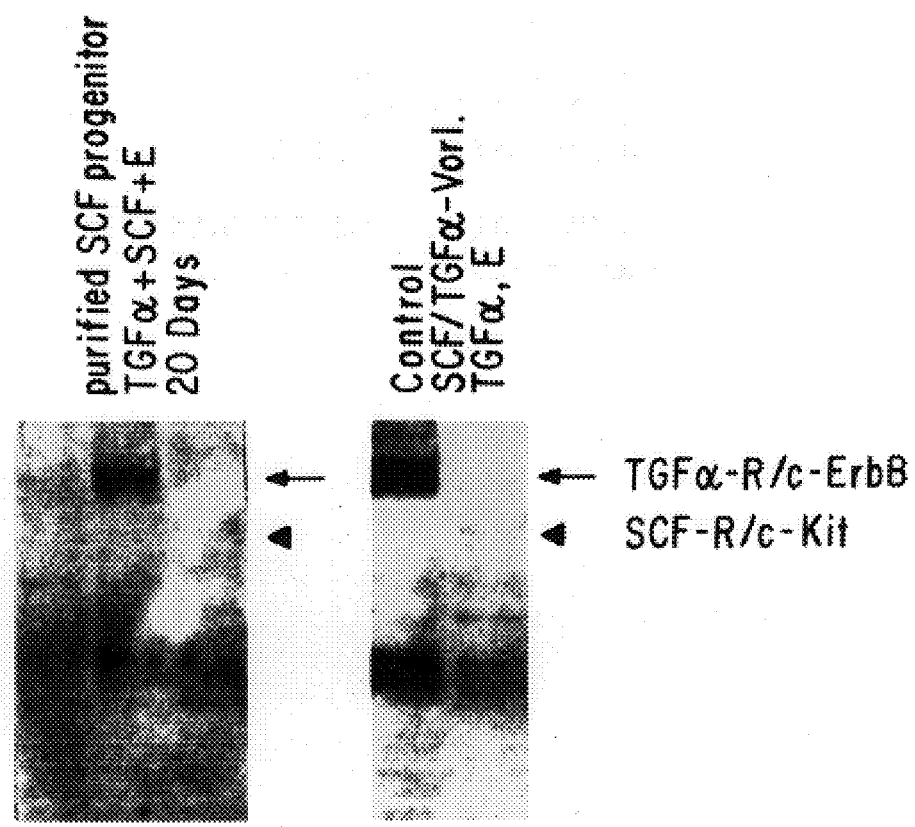
Figures 1, 2C, 2D:
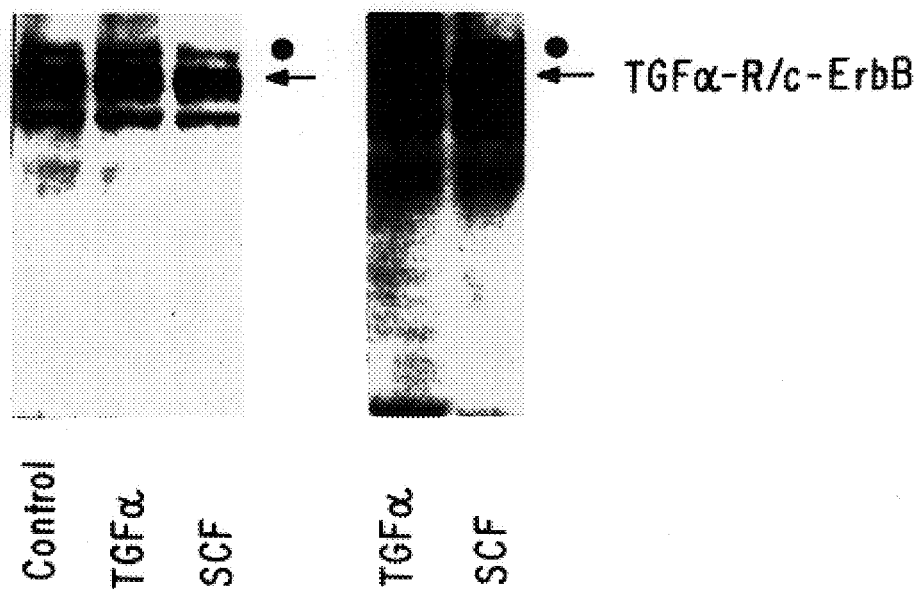

Similarly, the cells tested after 20 days (at this time they were growing both in TGFα plus oestradiol and also in SCF, TGFα and oestradiol) expressed increased amounts of TGFαR/c-ErbB, which was now clearly autophosphorylatable as a reaction to TGFα (FIG. 2C-1). Surprisingly, the cells were still expressing smaller amounts of TGFαR/c-ErbB than the control cells which had been cultivated from untreated bone marrow in TGFα plus oestradiol. (Schroeder et al., 1993; Hayman et al, 1993). The results obtained show that SCF precursors cultivated in TGFα, SCF and oestradiol express small amounts of TGFαR/c-ErbB even after 6 days and thereafter this expression increases continuously throughout the next 8 to 14 days.
b) Change in the growth factor dependency of SCF progenitors which proliferate in SCF, TGFα and oestradiol.

In order to confirm that the biochemically detected TGFαR/c-ErbB actually constitutes the bioactive receptor, the cells were additionally tested by [$^3$H]-thymidine incorporation assay to their reaction to SCF, TGFα and oestradiol as described by Hayman et al., 1993.

Figure 3A:
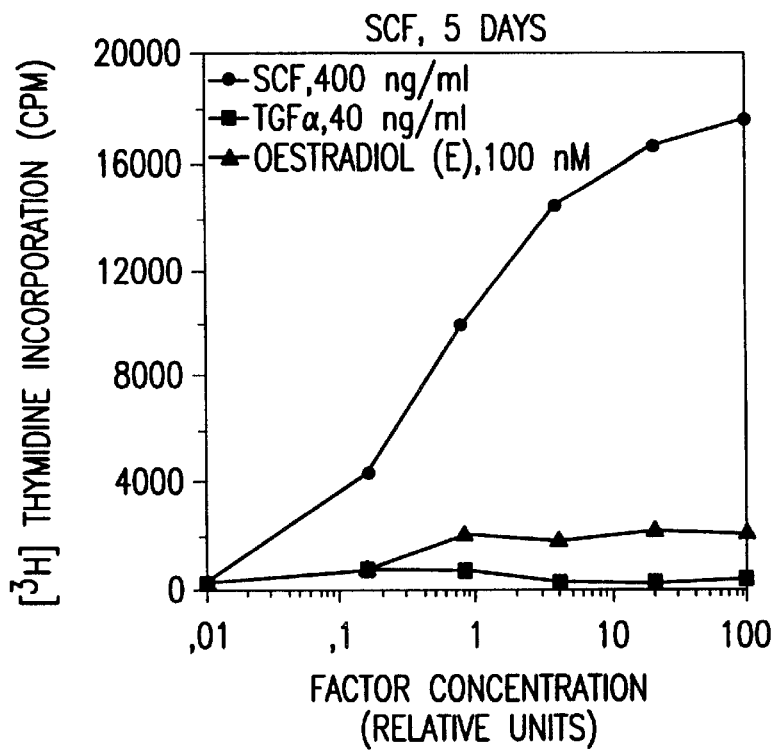
Figure 3B:
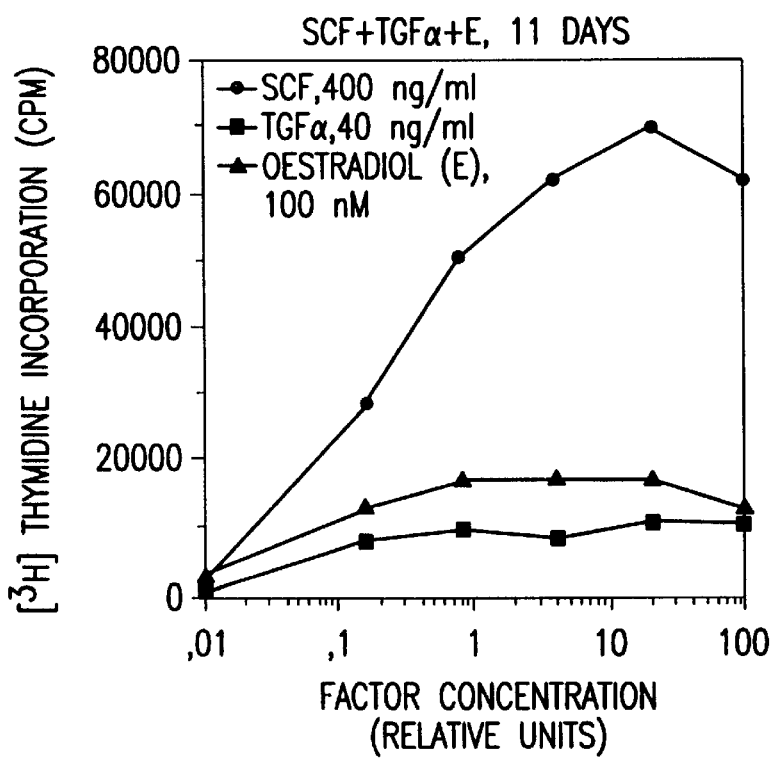
Figure 3C:
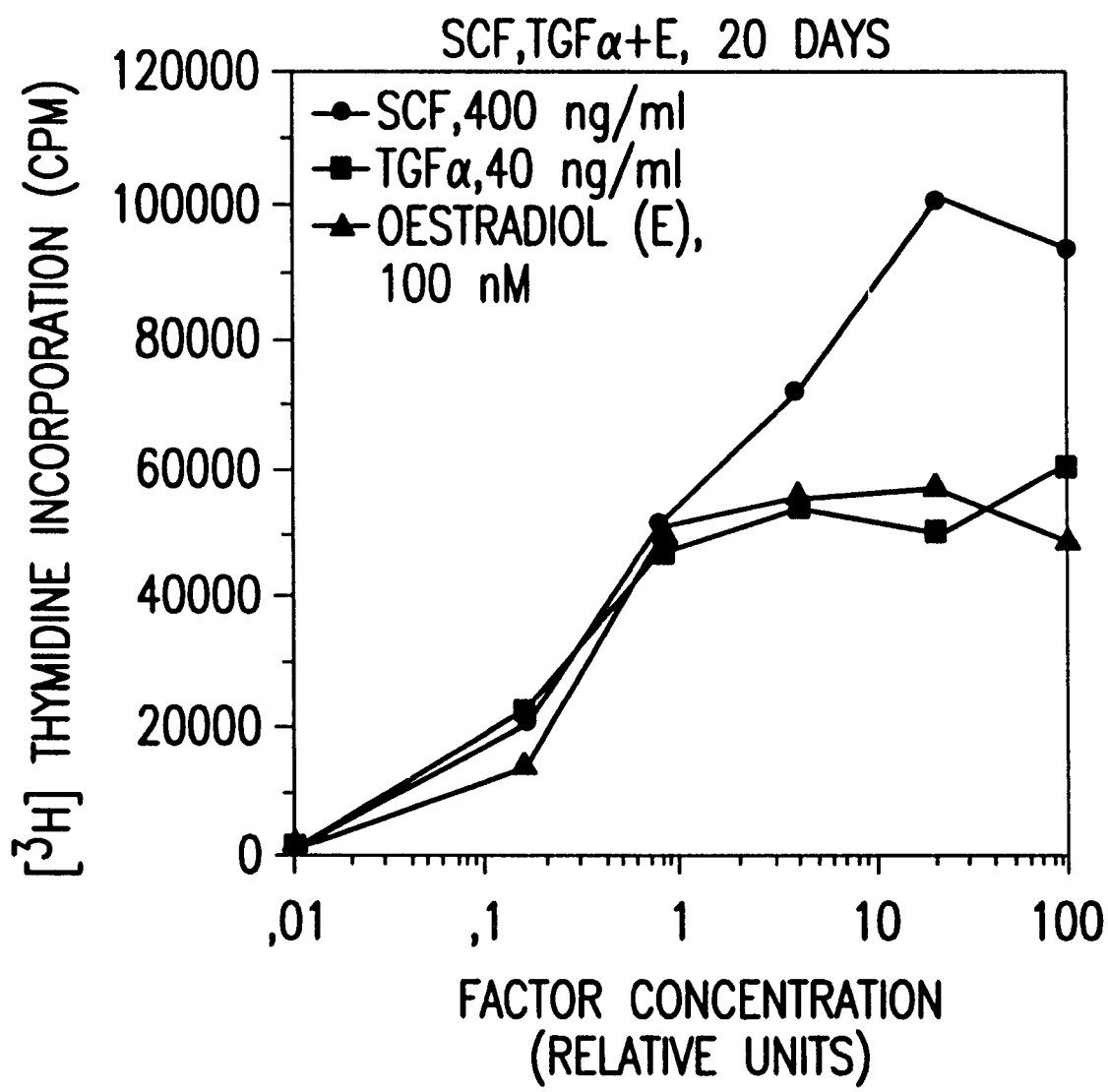

In order to do this, aliquots of a culture of SCF progenitors (5 days, FIG. 3A) or of cells which had been cultivated for 11 or 20 days in SCF, TGFα and oestradiol (FIGS. 3B and 3C) were investigated for their reaction to various factors (100 relative units correspond to the factor concentrations given under the symbols). It is apparent that the cells cultivated for 6 days in SCF, TGFα and oestradiol reacted to SCF and oestradiol as expected, whereas there was no detectable reaction to TGFα (FIG. 3A). After 11 days in contact with these factors, the reaction of the cells to SCF and oestradiol was unchanged, but now a weak but distinct reaction to TGFα could be made out (FIG. 3B). As expected, the cells cultivated for 20 days in SCF, TGFα an d oestradiol reacted strongly to all three factors showing no difference from the control-SCF/TGFα progenitors (FIG. 3C).

To summarise, the results obtained show that self-renewing SCF/TGFα progenitors can be cultivated efficiently from erythroid progenitors which initially react only to SCF and which lack both detectable quantities of TGFαR/c-ErbB and also the ability for longer lasting self-renewal.

EXAMPLE 3

Development of SCF/TGFα progenitors from SCF progenitors

In order to clarify the question of the origin of SCF/TGFα progenitors from cultures of SCF progenitors, the method of cloning by limiting dilution, hereinafter referred to as "LD cloning", was used. This method make s it possible to analyse the proliferation characteristics (and differentiation characteristics) of individual proliferating cells in a complex mixture of non-proliferating cells, because at a suitable dilution it is possible to monitor the development of individual proliferating cells in individual wells of cell culture plates (96 well plates). The success of such a method naturally depends on good cloning efficiency (10 to 50%) of the proliferating cells which are to be analysed, a criterion which is satisfied if the number of proliferating clones obtained is a linear function of the number of cells seeded out, up to a very few (1 to 10) clones per 96 well plate. (The fact that this criterion is satisfied for clarification of the present question has been demonstrated for SCF and SCF/TGFα progenitors by Hayman et al., 1993.)

Figures 1, 4A:
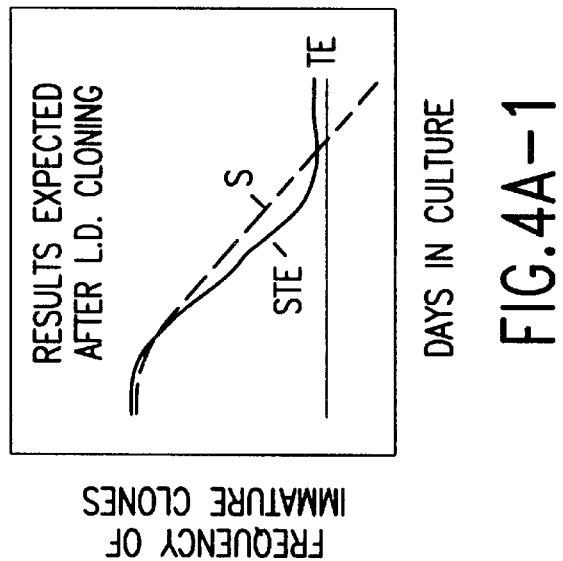
Figure 4A:
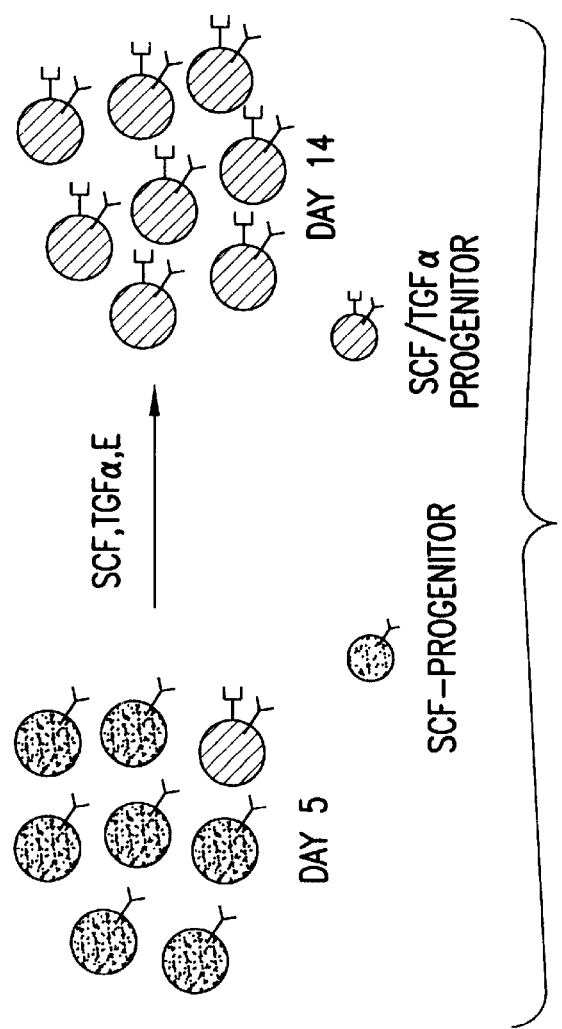
Figures 1, 4B:
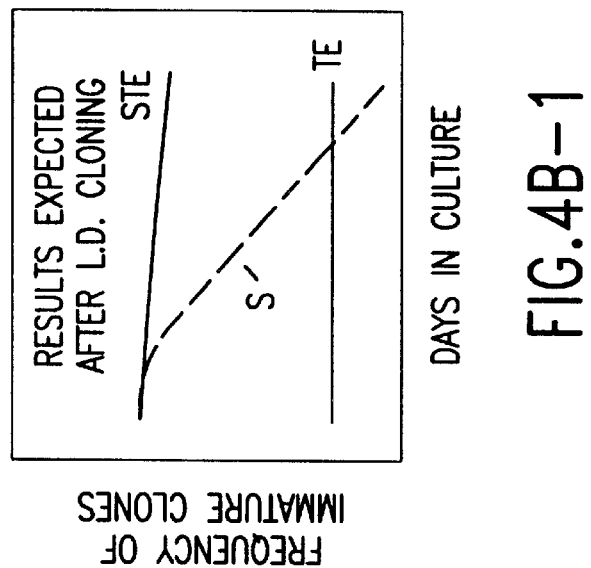
Figure 4B:
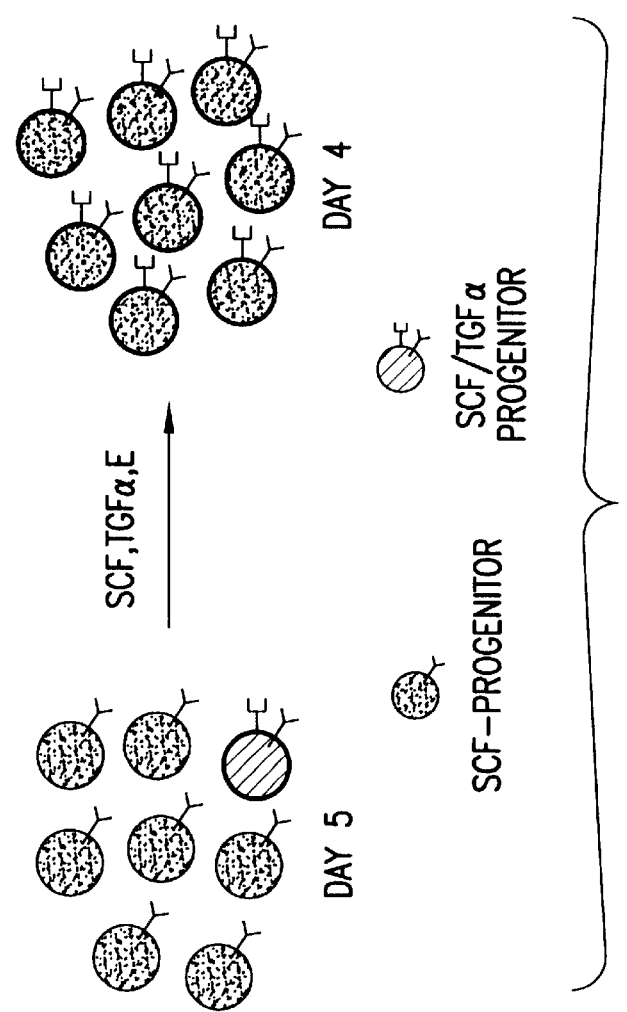

The question as to how the LD cloning occurs between the two possible models (selective outgrowth of rare SCF/TGFα progenitors from SCF progenitors or development of SCF progenitors into SCF/TGFα progenitors) is illustrated in FIGS. 4A-1 and 4B-1. FIGS. 4A and 4B diagrammatically show the model and FIGS. 4A-1 and 4B-1 show the expected results of LD cloning, whilst FIGS. 4A and 4A-1 show the model of the selective growth advantage of rare progenitors in SCF/TGFα and oestradiol and FIGS. 4B and 4B-1 show the alternative model based on a change in the differentiation programme of many or all progenitors. If, according to the first model, bone marrow contains both rare (one in 20,000) SCF/TGFα progenitors with the ability to renew themselves and stable c-ErbB expression, as well as additionally frequent (1 in 300) SCF progenitors which proliferate transiently in the presence of SCF but are capable neither of sustained self-renewal nor of expressing c-ErbB, SCF should induce numerous proliferating clones of SCF progenitors after 4 to 6 days. Thereafter, the number of proliferating clones should fall rapidly on account of differentiating or degenerating SCF progenitors. In TGFα plus oestradiol, a much smaller number of clones (1 in 20,000) should be obtained which should remain substantially constant on account of the long term self-renewal capacity of these clones. In the presence of all three factors (SCF, TGFα and oestradiol) the numbers of colonies should initially be as high as in SCF on its own but should thereafter fall to the level obtained with TGFα plus oestradiol (FIGS. 4A-1). According to the second model, bone marrow (and hence the SCF progenitors) contain only a few SCF/TGFα progenitors from the outset, whilst the majority of these cells develop from SCF progenitors in a slow process which requires the presence of SCF, TGFα, oestradiol (and chicken serum factors). One would therefore expect the frequency of the clones which develop in the presence of all three factors not to decrease in time or to decrease only slightly, which contrasts with the expected behaviour of such clones according to the first model (FIGS. 4B-1). The frequency of the clones developing, on the one hand, in the presence of SCF and, on the other hand, in the presence of TGFα and oestradiol should correspond to that of the first model (FIGS. 4B-1).

a) LD cloning of purified SCF progenitors

Purified three day old SCF progenitors were prepared as described by Hayman et al., 1993. The cells were then seeded in various concentrations (20 to 2,500 cells per well of the 96-well cell culture plate) into CFU-E medium containing either oestrogen alone (control) or SCF alone (plus the oestradiol antagonist ICI 164384 in order to suppress the oestradiol activity contained in the serum), or TGFα plus oestradiol or SCF, TGFα and oestradiol. To ensure good cloning efficiency 50 adherent myeloid cells were seeded into all the wells as a feed layer (the myeloid cells were obtained by preparing bone marrow cells and seeding them out at a rate of $50 \times 10^6$ cells/ml per 100 mm dish and treating them with 10 ng/ml of cMGF and SCF. During the first 2 to 3 days the non-adherent or only slightly adherent cells were extended and then allowed to adhere in a larger dish.) Immature healthy colonies were counted 4, 9 and 11 days after the seeding of the cells (corresponding to a total age of the cells of. 7, 12 and 14 days).

Figure 5A:
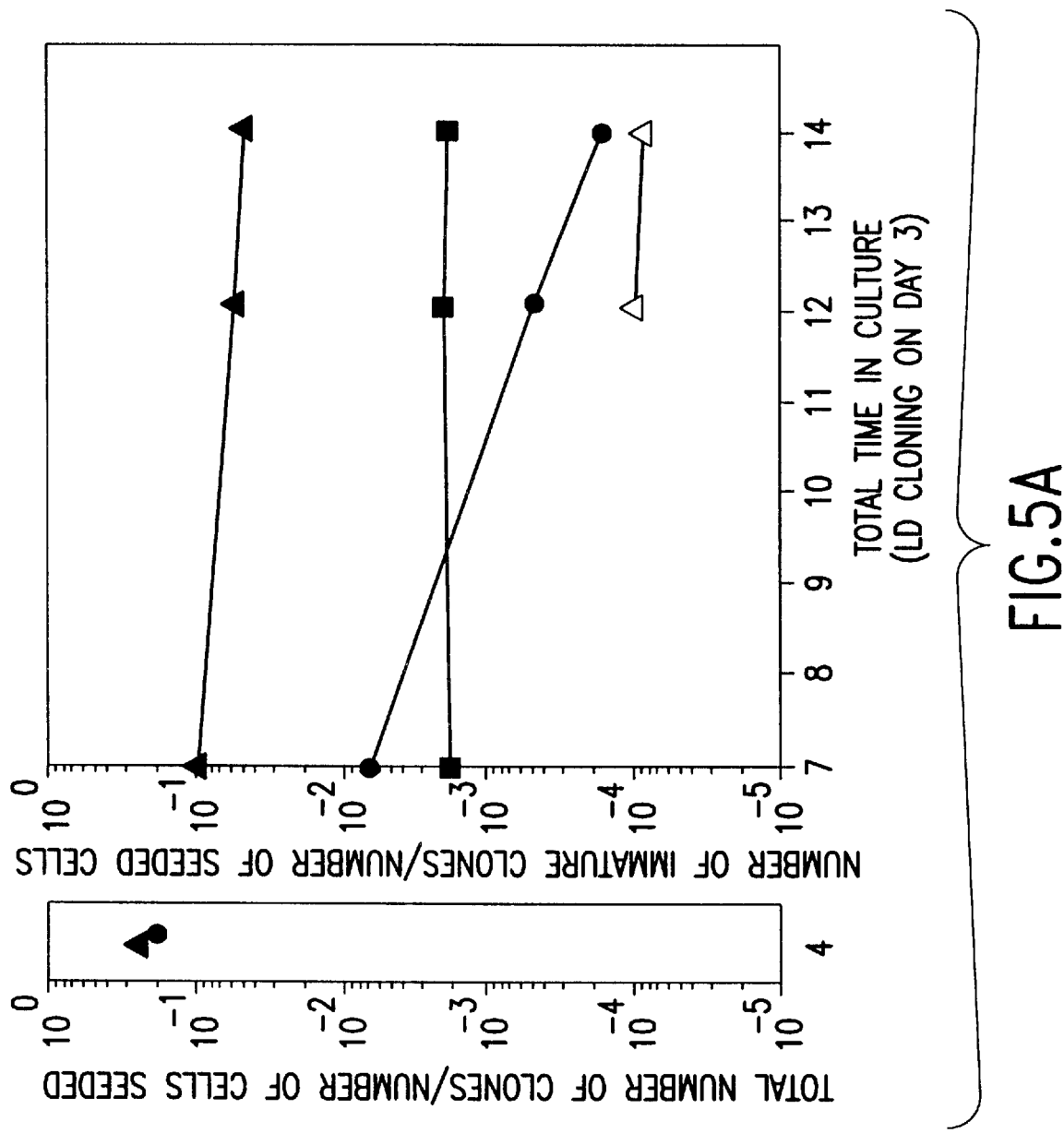
FIGS. 5A and 5B: Development of SCF/TGFα progenitors from SCF progenitors

The results are shown in FIG. 5A (apart from the controls in FIG. 5, where very few colonies were obtained, the frequencies found are the results of counting more than 100 colonies of at least two different cell dilutions). As a control, first the total cloning efficiency (undifferentiated plus differentiated colonies) was determined, obtained 2 to 3 days after seeding with the purified SCF progenitors in the various media (FIG. 5A, left panel). It will be seen that in the presence of SCF cloning rates of 10 to 20% were obtained, irrespective of the presence of oestradiol or TGFα. In the media which contained TGFα plus oestradiol, or in the controls which contained only oestradiol, the few visible colonies at this time were too small to be counted.

More conclusive were the results obtained with colonies which contained more than 50% healthy, immature cells. On day 7, the number of clones cultivated in SCF alone had already fallen to $<10^{-2}$, whereas the clones cultivated in SCF, TGFα and oestradiol were still present in a frequency of $10^{-1}$. The frequency of the clones grown in TGFα plus oestradiol was even smaller ($2 \times 10^3$), whereas the clones in the oestradiol control samples were not yet visible.

Further behaviour of the clones grown in the various media supported the hypothesis that SCF/TGFα progenitors develop from SCF progenitors. Immature clones growing in SCF alone fell to $3 \times 10^{-4}$ or $1 \times 10^{-4}$ after 12 to 14 days, approximating to the background level ($5 \times 10^{-5}$) of the colonies grown in oestradiol alone. As expected, the small number of colonies which had been grown in TGFα plus oestrogen ($2 \times 10^{-3}$) did not change over time. In accordance with the finding that SCF progenitors can develop into SCF/TGFα progenitors (FIGS. 4B and 4B-1) a considerable proportion of the clones grown in SCF, TGFα and oestradiol remained immature and capable of proliferation, whilst the frequency decreased only slightly (from $9 \times 10^{-2}$ on day 7 to $5 \times 10^{-2}$ on day 14; FIG. 5A).

b) LD cloning of normal bone marrow cells

To rule out that SCF progenitors with the ability to acquire self-renewing potential in SCF, TGFα and oestradiol had been preselected by in vitro cloning before the LD cloning, tests were carried out with fresh untreated bone marrow cells to confirm the results obtained in a). In particular it was intended to determine whether erythroid progenitors with self-renewing potential could indeed be generated from single cells at frequencies approaching those of SCF progenitors (one progenitor in 3,000–5,000; Hayman et al., 1993) if grown in all three factors, whilst remaining rare (1 in 15,000) if grown in TGFα plus oestradiol alone.

Figure 5B:
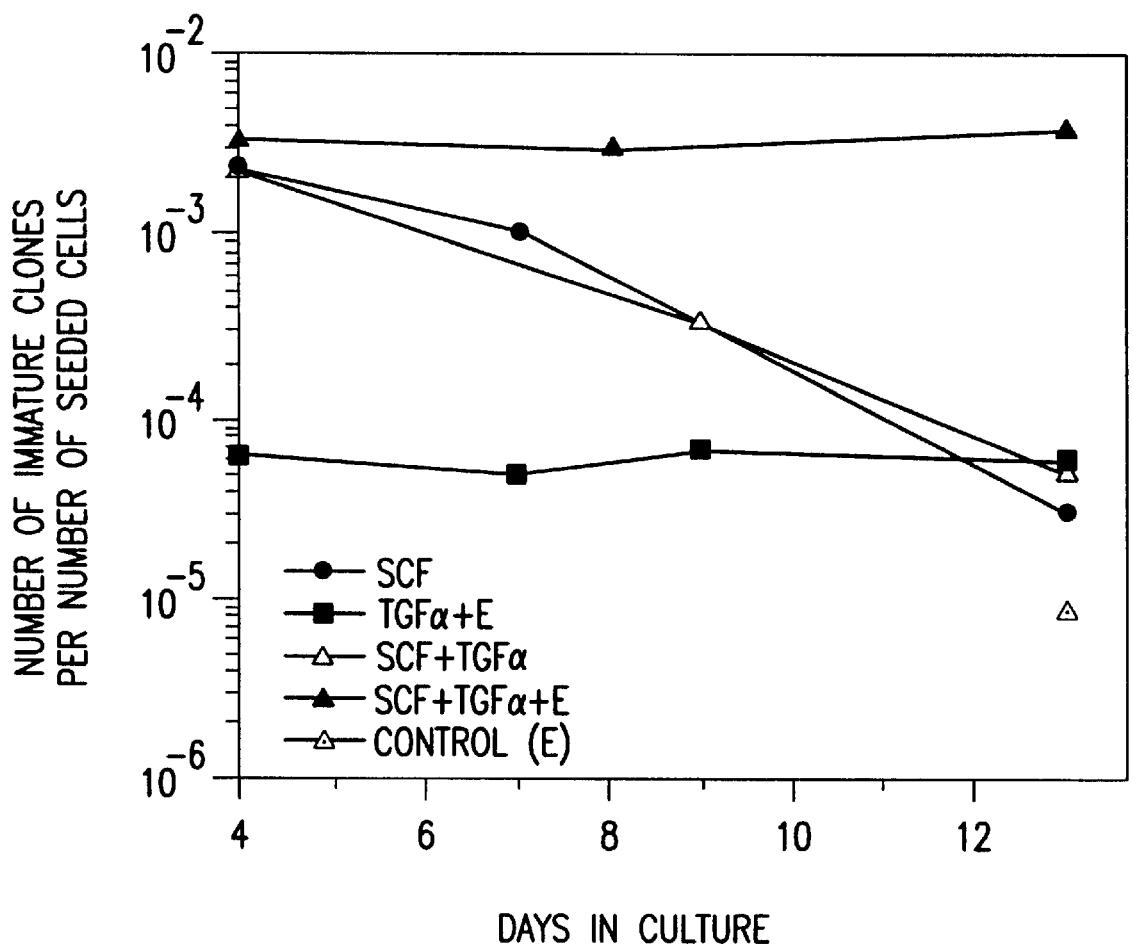

Normal bone marrow cells prepared as described by Hayman et al., 1993 were seeded into CFU-E medium containing various factor combinations at 4 different cell dilutions (500, 2,000, 6,000, 15,000) in a range of from 500 to 15,000 cells per well, and immature colonies (containing more than 50% round proliferating cells) were counted at various times after seeding. The results are shown in FIG. 5B: after 4 days, the cells grown in SCF formed colonies with a frequency of $3 \times 10^{-2}$ to $5 \times 10^{-2}$. Thereafter, the frequency of immature colonies decreased progressively, reaching a frequency of $2 \times 10^{-5}$ after 13 days. An increasing proportion of cells underwent differentiation and then apoptosis. As expected, the clones grown in TGFα plus oestradiol were rare from the beginning ($6 \times 10^{-5}$ to $8 \times 10^{-5}$) but the frequency remained substantially constant during the experiment. On the other hand, the clones grown in SCF, TGFα plus oestradiol were found on day 4, 8 and 13 with a frequency of $3 \times 10^{-2}$ to $5 \times 10^{-2}$. Thus, the three factors SCF, TGFα and oestradiol can actually induce the outgrowth of immature colonies from bone marrow with a frequency corresponding to that of SCF progenitors after 4 days and similar to the frequency of cells in normal chicken bone marrow which are capable of forming CFU-E colonies. Finally, it was to be established whether all three factors are actually necessary to induce the outgrowth of immature LD clones with a high frequency. In media containing individual factors (oestradiol alone, TGFα or SCF plus ICI 164384 in order to suppress the endogenous serum oestradiol) only very small numbers of immature clones were obtained (about 10–5). In TGFα plus SCF without oestradiol the clones behaved exactly as in SCF on its own, i.e. they were frequent on day 4 and then decreased progressively (FIG. 5B). Surprisingly, the clones cultivated in SCF plus oestradiol remained immature for much longer than those cultivated in SCF alone, but grew much more slowly compared with clones cultivated in TGFα plus oestrogen or SCF or in TGFα plus oestrogen. Since these clones bore no resemblance to the typical SCF/TGFα progenitors (in terms of both c-ErbB expression and in vitro lifespan, cf. Example 4), they were not investigated further.

EXAMPLE 4

Investigation of the in vitro lifespan and expression of TGFαR/c-ErbB of SCF/TGFα progenitors developed from SCF progenitors In order to investigate whether the immature clones obtained by LD cloning of normal bone marrow cells or SCF progenitors in SCF, TGFα plus oestradiol with great frequency were actually typical SCF/TGFα progenitors, they were examined both in terms of their in vitro life span and also their expression of TGFαR/c-ErbB and their proliferative response to TGFα and other factors. The tests were carried out in comparison with cells grown only in TGFα plus oestradiol and also with cells from SCF/TGFα progenitor mass cultures.

a) Determining the life span

In order to analysis the in vitro lifespan, 10 to 12 healthy immature colonies cultivated in SCF, TGFα and oestradiol (obtained from 96 well plates with 500 seeded out cells) or grown in TGFα plus oestradiol (from plates with 15,000 cells) were isolated, suspended and expanded in their respective media until $20 \times 10^6$ cells were obtained in a 100 mm dish or the cells stopped growing because they had reached their clone specific in vitro lifespan (cell senescence). The growing clones were then passaged (diluted and transferred with fresh medium into new culture dishes) until they also aged. All immature colonies obtained after 13 days' growth in SCF alone (6 colonies), as well as those from the control cultures (oestradiol alone: 5 colonies; SCF alone: 5 colonies; TGFα alone: 3 colonies; SCF plus TGFα: 8 colonies; SCF plus oestradiol: >15 colonies) were treated similarly.

Clones which exhibited the lifespan predicted for the SCF/TGFα progenitors were obtained only in SCF, TGFα plus oestradiol and, as expected, in TGFα plus oestradiol. 8 out of 12 of the clones grown with high frequency in SCF, TGFα plus oestradiol had a lifespan of 23 to over 28 generations (the remaining 4 had a lifespan of 12 to 15 generations). 7 out of 10 clones which had grown in TGFα plus oestradiol with a lower frequency had a similarly high life expectancy (23 to 31 generations; the lifespan of the remaining 3 was 15 to 17 doublings). This clearly shows that the life expectancy of SCF/TGFα progenitors which had developed from SCF-progenitors in the presence of SCF, TGFα plus oestradiol, is identical to those of genuine SCF/TGFα progenitors. None of the colonies which had formed in the presence of individual factors or SCF plus TGFα had a lifespan of more than 12 to 16 generations. One clone obtained in SCF plus oestradiol could be cultivated up to the 22nd generation whereas 9 others had a short lifespan (12 to 18 generations). However, this clone grew at reduced speed, expressed very small amounts of TGFαR/c-ErbB and did not react to TGFα in a growth factor assay. It can therefore be assumed that these cells are more likely to be an abnormal cell clone than actual SCF/TGFα progenitors.

b) Expression of TGFαxR/c-ErbB and response to TGFα and other growth factors

Figure 6A:
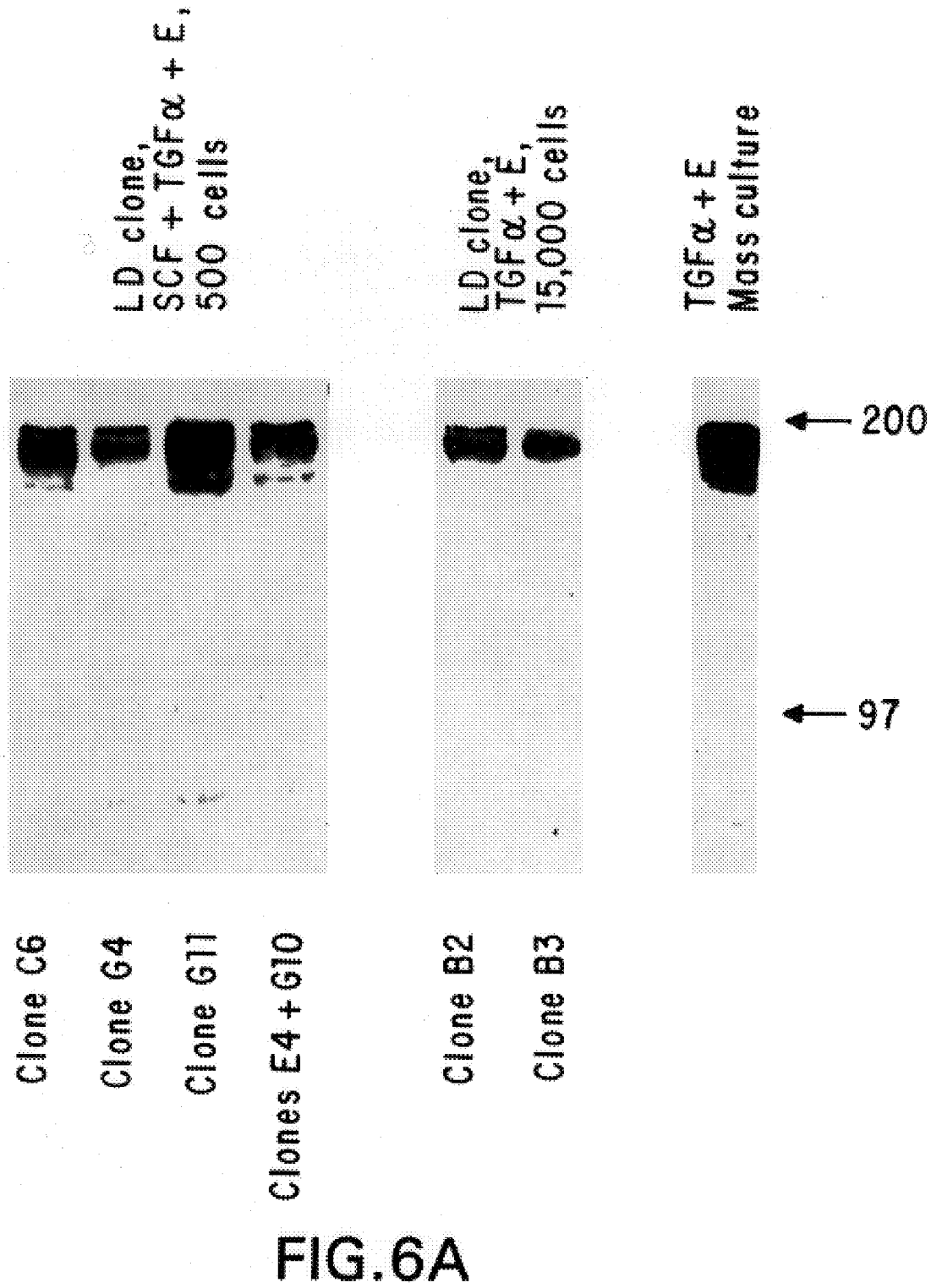
FIGS. 6A–6C: LD clones grown in SCF, TGFα and oestradiol correspond to SCF/TGFα progenitors: expression of bioactive c-ErbB and proliferation reaction to TGFα

To determine whether the LD clones obtained with high frequency in SCF, TGFα plus oestradiol express TGFαR/c-ErbB in similar amounts to SCF/TGFα progenitors grown in TGFα plus oestradiol, all the factors were removed overnight from the cells of 5 LD clones (2 clones were combined because of the low number of cells) cultivated in all three factors, from 2 clones cultivated in TGFα plus oestradiol and from an SCF/TGFα progenitor mass culture, then the cells were lysed and investigated by Western blot using anti-c-ErbB antibodies for TGFαR/c-ErbB expression. FIGS. 6A, and B (c-ErbB expression of LD clones from bone marrow) clearly shows that somewhat fluctuating but similar quantities of TGFαR/c-ErbB were expressed in all three cell types, which again indicates that the erythroblast clones formed from SCF progenitors in the presence of all three factors are genuine SCF/TGFα progenitors.

Figure 6B:
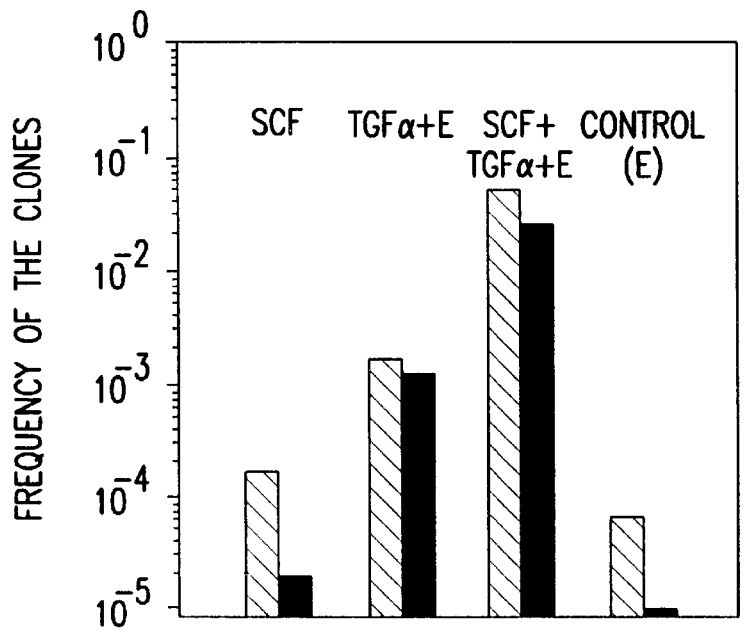

In order to determine more quantitively the extent to which the large number of LD clones obtained in the presence of the three factors is similar to SCF/TGFα progenitors, another method was used: LD clones induced from purified SCF progenitors by cultivation in the three factors (see FIG. 5B) were counted on day 13 and the plates on which the majority of wells contained an immature culture were selected. Then the contents of all the wells were suspended, washed in medium without factors and transferred into new 96 well plates containing medium supplemented with TGFα plus oestradiol. Control LD clones obtained from TGFα plus oestradiol, SCF on its own and oestradiol on its own, were treated similarly. 3 days later (day 16) the clones were investigated for their proliferative capacity by measuring the [$^3$H]thymidine incorporation (wells with a number of counts 5 times (for the individual colonies) or 10 times (2 or more colonies) above the background level were counted as positive. From this analysis it was possible to calculate the frequency of the thymidine-incorporating clones (FIG. 6B, panel B; the filled-in bars indicate the thymidine-incorporating clones; the shaded bars indicate all the clones). The data obtained show that essentially all healthy immature clones which had been cultivated in TGFα plus oestradiol and identified on day 13 incorporated thymidine on day 16, confirming that they was still actively proliferating. The same was true of more than 50% of the (30 times more numerous) clones which had been generated in the presence of all three factors. By contrast, fewer than 10% of the few clones which had survived after 13 days in SCF alone, incorporated thymidine, whereas the similarly rare clones which had grown out in the presence of oestradiol alone showed no proliferation whatever in TGFα plus oestradiol. This led one to assume that the clones generated in the controls are not typical SCF/TGFα progenitors, a finding which is confirmed by their short in vitro lifespan (see a)).

Figure 6C:
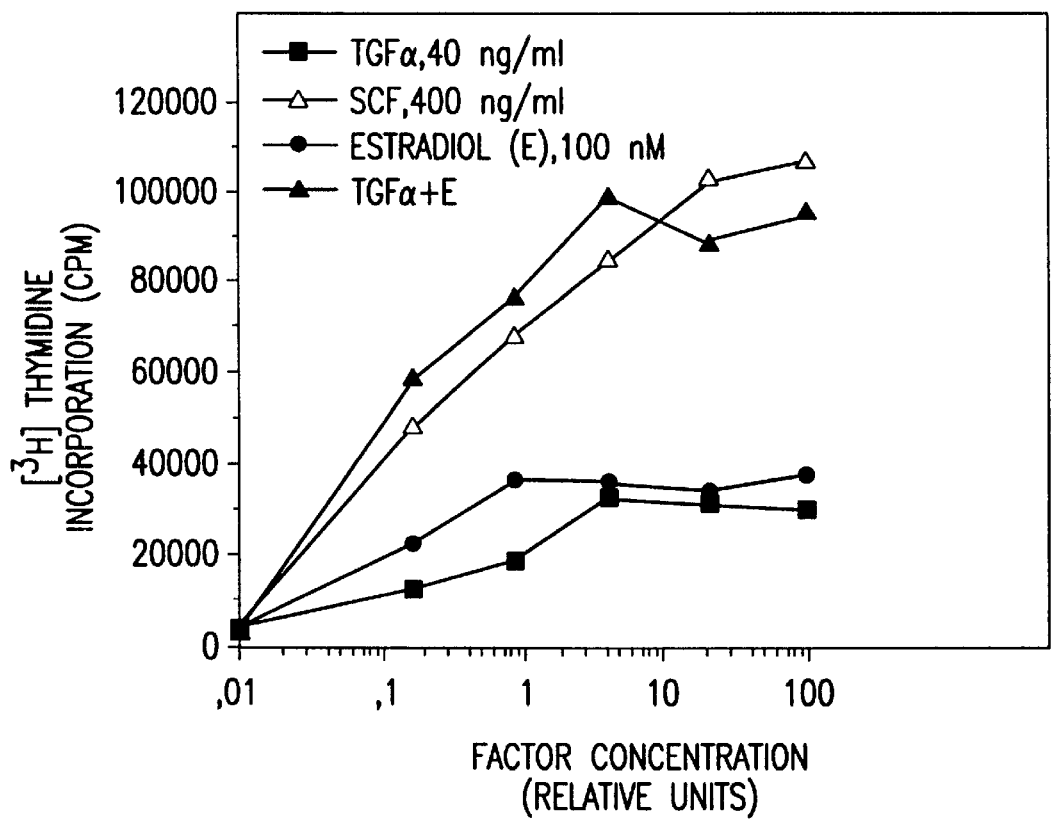

Finally, the intention was to confirm that the LD clones grown from SCF progenitors at high frequency in the presence of all three factors demonstrate a similar dependency on SCF, TGFα and oestradiol to SCF/TGFα progenitors. FIG. 6C, shows that an LD clone designated C6 (cf. FIG. 6A,) showed a clear, concentration-dependent reaction to all three factors, which nearly corresponded to the characteristics of an SCF progenitor mass culture which had been cultivated for 20 days in the presence of the three factors (see FIG. 3C) or SCF/TGFα progenitors cultivated in TGFα plus oestradiol alone.

EXAMPLE 5

Definition of the factors which are necessary to change the differentiation programme of SCF progenitors into SCF/TGFα progenitors The results obtained in th e p receding Examples show that SCF progenitors can develop into SCF/TGFα progenitors, i.e. they acquire the capacity for both sustained self-renewal and also for the expression of endogenous TGFαR/c-ErbB when cultivated in the presence of the three factors. However, the fact that such cultures are critically dependent on the presence of chicken serum which may contain small concentrations of TGFα, SCF and/or oestradiol as well as additional uncharacterised factors, set limits on the evaluation of the data and raised a number of questions. It remained unclear whether SCF/TGFα progenitors required small concentrations of SCF, which are certainly present in chicken serum. In addition, SCF progenitors could require small quantities of a chicken factor which functionally replaces TGFα and which is also contained in chicken serum. Secondly, it was unclear at what time during the development of SCF/TGFα progenitors from SCF progenitors the various factors were required. And finally there was the question as to which factor or factors in chicken serum is or are required for the TGFα/oestradiol-induced outgrowth of SCF/TGFα progenitors from bone marrow and whether this factor or these factors constitute a new activity or a known factor, e.g: SCF.

Figure 7A:
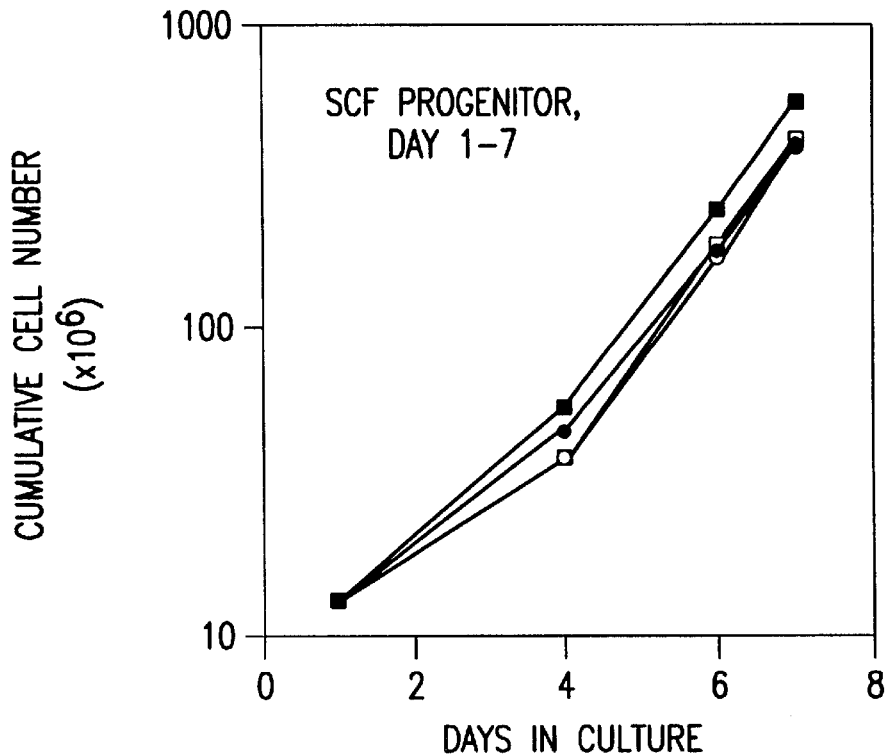
FIGS. 7A–7C: A factor in chicken serum facilitates the development of SCF progenitors to SCF/TGFα progenitors
Figure 7B:
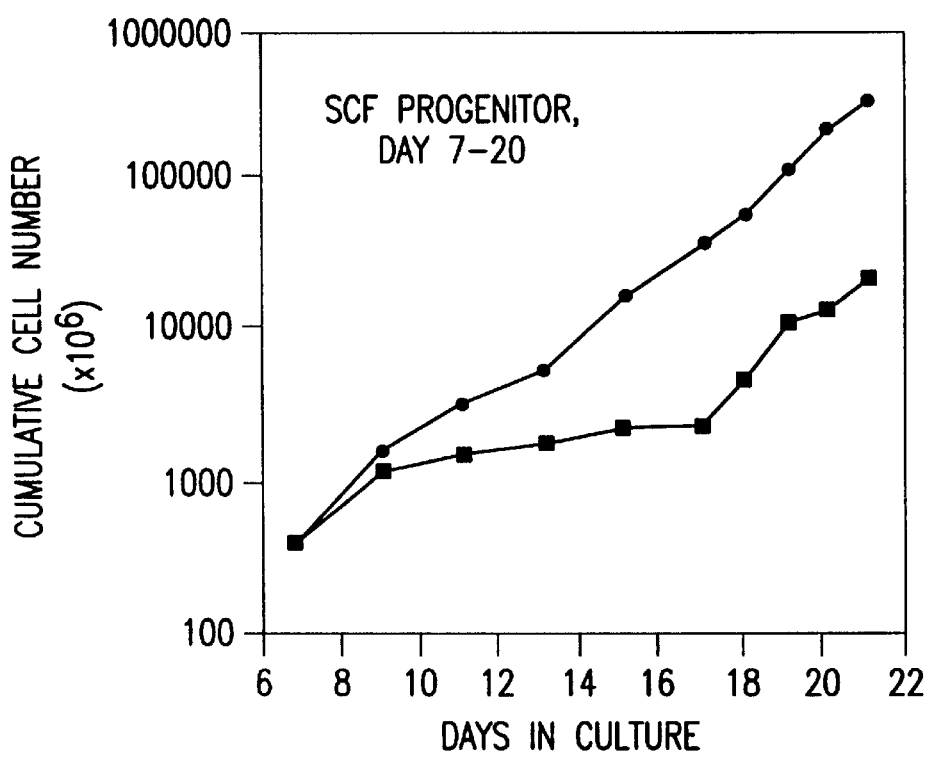
Figure 7C:
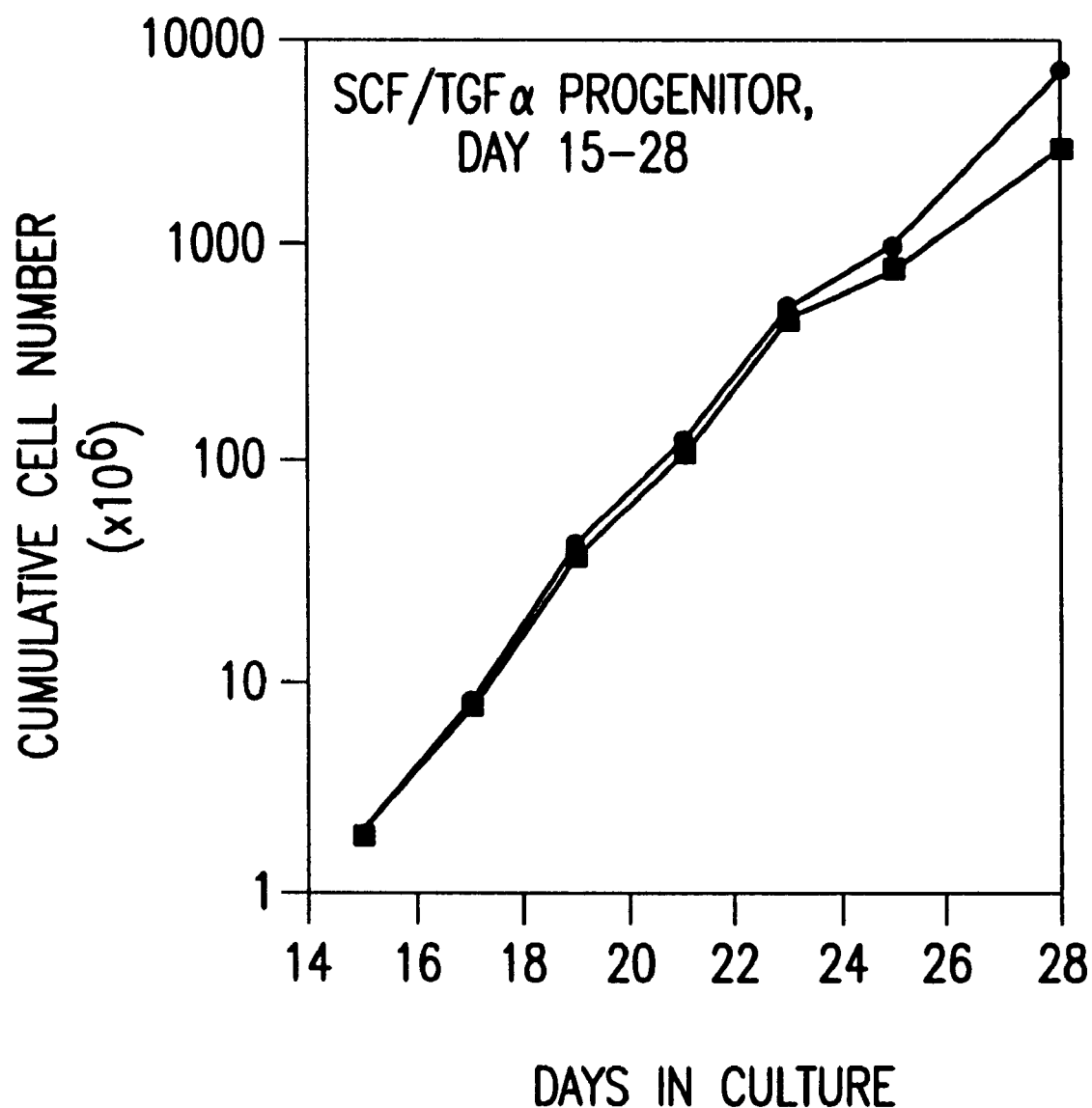

In order to answer these questions it was necessary to prepare a batch of chicken serum which was substantially free from endogenous growth factor and hormone activities but which still fully permitted the growth of factor-dependent cells when the necessary growth factors were added from outside. Initial tests had shown that chicken serum treated with animal charcoal (Schroeder et al., 1992) strongly inhibited the TGFα/oestradiol-induced outgrowth of SCF/TGFα progenitors (although did not completely suppress it), but did not affect the growth rate of these progenitors once they were established. Therefore, chicken serum which had been thoroughly freed from endogenous hormones-and factors by freon treatment and subsequent three time treatment with animal charcoal (Schroeder et al., 1992) was used for the present experiments (this depleted serum is referred to hereinafter as "treated chicken serum". Bone marrow cells were cultivated in CFU-E medium containing freon-treated foetal calf serum and either untreated chicken serum or treated chicken serum. The cells were cultivated either in SCF alone or in SCF, TGFα and oestradiol and counted at the times specified in FIGS. 7A–7C which shows the cumulative cell numbers determined as in Example 1. CFU-E medium prepared with the treated chicken serum (in FIGS. 7A–7C the open squares indicate purified chicken serum plus SCF; solid squares indicate purified chicken serum plus oestradiol; open circles denote normal chicken serum plus SCF and solid circles indicate normal chicken serum with oestradiol), made it possible for SCF progenitors to grow to the same extent as the control medium with untreated chicken serum, irrespective of whether the cells were cultivated in SCF alone or in SCF, TGFα plus oestradiol (FIG. 7A,). Moreover, there was no effect on the proliferation rate of 15 day old SCF/TGFα progenitor cultures, apart from a slight effect when the cells began to age (FIG. 7C). Surprisingly, however, the treated chicken serum slowed down the development of SCF progenitors into SCF/TGFα progenitors in the presence of SCF, TGFα and oestradiol (FIG. 7B). After their delayed appearance, however, the SCF/TGFα progenitors generated in treated chicken serum grew at the same rate as the control cells in untreated chicken serum which had formed at least 5 days earlier (FIG. 7B).

These observations permit numerous conclusions: firstly, chicken serum contains an additional activity which promotes the development of SCF progenitors into SCF/TGFα progenitors. And secondly this activity is important for the switch in development, but does not affect the proliferation of SCF progenitors before the change nor is important for the proliferation of already established SCF/TGFα progenitors. The availability of a suitably treated chicken serum also made it possible to investigate at what time during the development of SCF/TGFα progenitors the known factors are required. 3 day old purified SCF progenitors grew at comparable speed in SCF plus TGFα, independently of the presence or absence of oestradiol (FIG. 8A, the oestradiol present in the normal chicken serum used was again suppressed with ICI 164384). Thus, oestradiol has no effect on the early proliferation of SCF progenitors. The fact that they grew at the same rate in media containing treated chicken serum, SCF and oestradiol with or without TGFα shows that TGFα is also dispensable and that the only factor required by early SCF progenitors is SCF.

Figure 8A:
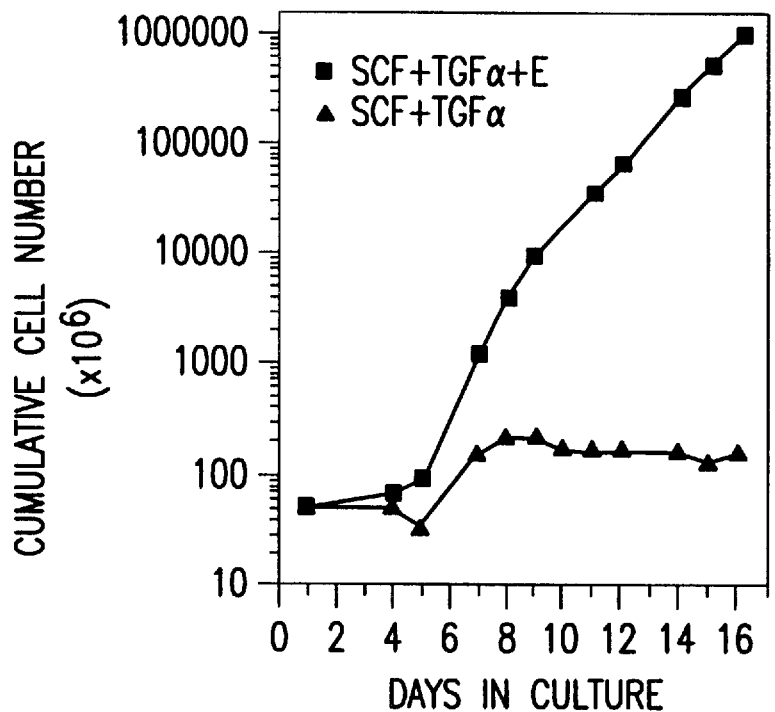
FIGS. 8A and 8B: Need for oestradiol and SCF during the development of SCF/TGFα progenitors-from SCF. progenitors
Figure 8B:
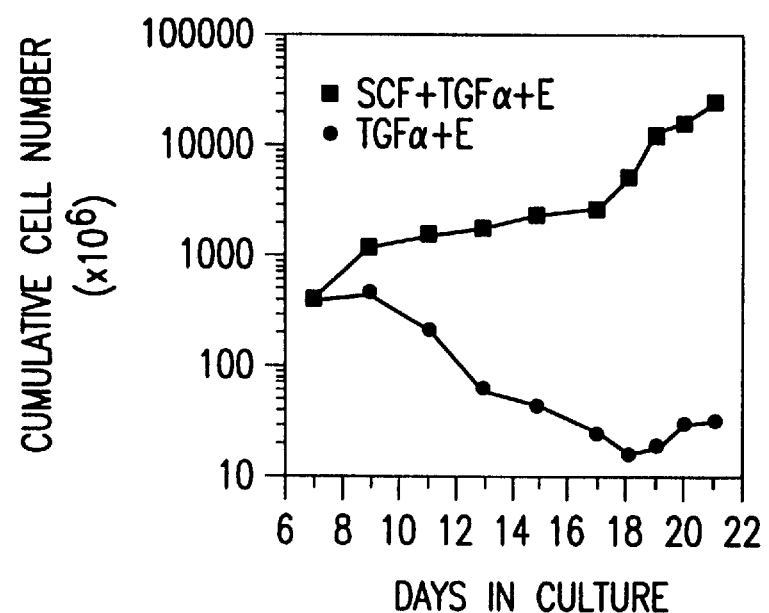

A different pattern of requirements of growth factors is produced during the change in the differentiation programme. As shown in FIG. 8A, cells kept in SCF plus TGFα without oestradiol irreversibly ceased to proliferate around day 8 to 10, indicating that oestradiol is necessary for the switch. Earlier results indicate that it is also essential for the proliferation of established SCF/TGFα progenitors (Schroeder et al., 1993). Another group of experiments clearly shows that SCF is necessary during the change in the differentiation programme. 6 day old SCF progenitors established in media containing treated chicken serum and SCF are able to develop with low efficiency into SCF/TGFα progenitors if they are further cultivated in treated chicken serum which contains all three exogenous factors. However, if they are given only TGFα and oestradiol, under otherwise identical conditions, they lose this ability entirely (FIG. 8B).

Therefore, the development of SCF/TGFα progenitors is dependent on the presence of SCF during the change in the differentiation programme, whilst, once established, these progenitors are independent of SCF (see FIG. 7C, and below). Finally, SCF progenitors do not require any TGFα (FIG. 7A,) but no formation of SCF/TGFα progenitors occurs in the absence thereof, even if untreated chicken serum is used (Schroeder et al., 1993). To sum up, the tests carried out lead to the following conclusion: the joint presence of SCF, TGFα and oestradiol is necessary for the development of SCF/TGFα progenitors from SCF progenitors, whilst an unknown further activity in chicken serum increases the efficiency of their formation.

Figure 8C:
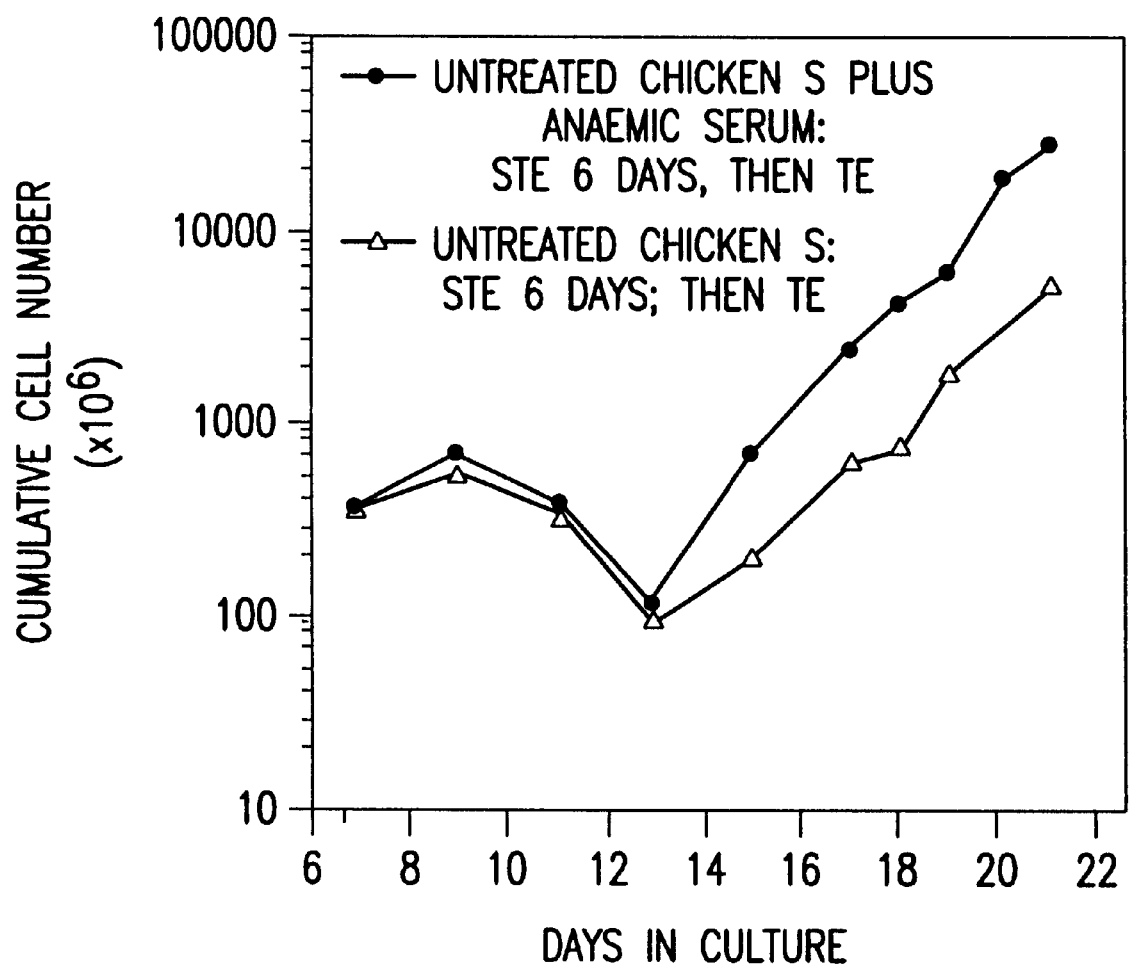
FIG. 8C: Acceleration of the development of SCF to SCF/TGFα progenitors using anaemic chicken serum

Some data from guide experiments which were additionally carried out lead one to suppose that this activity might be chicken erythropoietin, but they do not prove this. It was found that anaemic serum in growth factor assays strongly stimulates the proliferation of SCF/TGFα progenitors; a more important finding was the fact that anaemic serum increased the growth rate of SCF/TGFα progenitors during and after the establishment thereof, even when these cells were exposed to normal chicken serum plus SCF, TGFot and oestradiol ("STE") (FIG. 8C,).

Finally, erythroblasts which had been stimulated to self-renewal by means of a retrovirus stably expressed c-ErbB, i.e. an exogenous tyrosine kinase and which expressed the murine erythropoietin receptor after infection with another retrovirus, were able to be stimulated in their proliferation rate threefold or more by means of human recombinant erythropoietin (EPO).

EXAMPLE 6

Identification of two factors from chicken serum which speed up the conversion[]of SCF progenitors into SCF/TGFα progenitors or are necessary for their growth a) Ligands of the glucocorticoid receptor (e.g. dexamethasone) belong to the factors from chicken serum which SCF progenitors require for their development into SCF/TGFα progenitors The previous Example showed that the development of SCF progenitors into SCF/TGFα progenitors required, in addition to SCF, TGFα and oestradiol, other undefined factors from chicken serum which could be eliminated by activated charcoal treatment of the serum. In the presence of a chicken 'serum treated with activated charcoal, the development into SCF/TGFα progenitors does not occur or takes place very inefficiently.

Since steroid hormones in particular are eliminated by activated charcoal treatment of serum, other steroid hormones apart from oestradiol were investigated for their activity during the conversion of the differentiation programme of normal erythroid cells. First of all, ligands of the glucocorticoid receptor were tested, since a deficiency of glucocorticoids in humans lead inter alia to anaemia and prevents the DMSO-induced differentiation in Friend-erythroleukaemia cells in the mouse. Preliminary experiments showed 1) that SCF cells do not require DMSO for their temporary self-renewal and 2) established SCF/TGFα cells require small concentrations of glucocorticoids for their growth. The cells do not grow when cultivated in the presence of TGFα and oestradiol in media in which both the foetal calf serum and the chicken serum have been treated with activated charcoal. If an additional $1 \times 10^{-6}$M dexamethasone is added to the same medium, the cells are stimulated to grow at normal speed. The cells may also fail to grow even in untreated media if a glucocorticoid antagonist is added as well as the TGFα and oestradiol.

In order to test directly whether glucocorticoids (dexamethasone) speed up the conversion of SCF into SCF/TGFα progenitors, an experiment was carried out in which SCF progenitors were exposed to various factor mixtures for a short time (4 days, day 3–7 after isolation of the bone marrow, hereinafter referred to as the induction period) (see FIGS. 9A and 9B). The cells were then washed and seeded into medium containing only TGFα and oestradiol (TE medium). In this medium, only c-ErbB expressing, fully developed SCF/TGFα progenitors can grow, but not SCF progenitors or cells at an early stage of development into SCF/TGFα progenitors (see Example 5). The results are shown in FIGS. 9A and 9B.

As a negative control, the cells (4 day old SCF progenitors)were cultivated during the induction period in SCF plus medium with activated charcoal-treated sera (foetal calf serum and chicken serum). After switching to TE medium, no cell growth could be observed for a long time. Not until 9–10 days after the switch to TE medium had passed did SCF/TGFα progenitors grow out (FIGS. 9A and 9B, white lozenges) which presumably derived from cells already present in the bone marrow as SCF/TGFα progenitors (see Example 5).

Figure 9A:
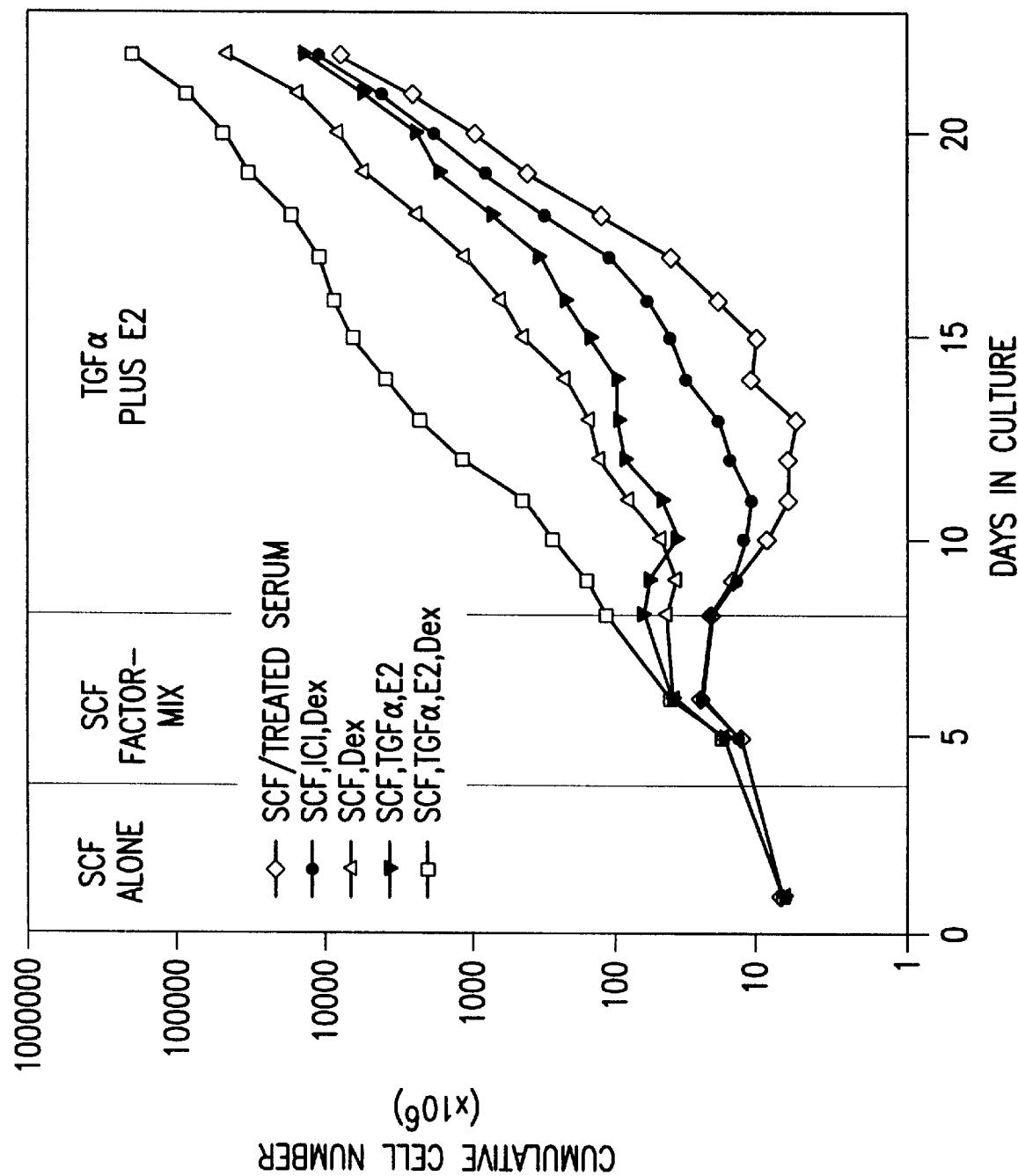
FIG. 9A: Speeding up the conversion of SCF progenitors into SCF/TGFα progenitors using dexamethasone
Figure 9B:
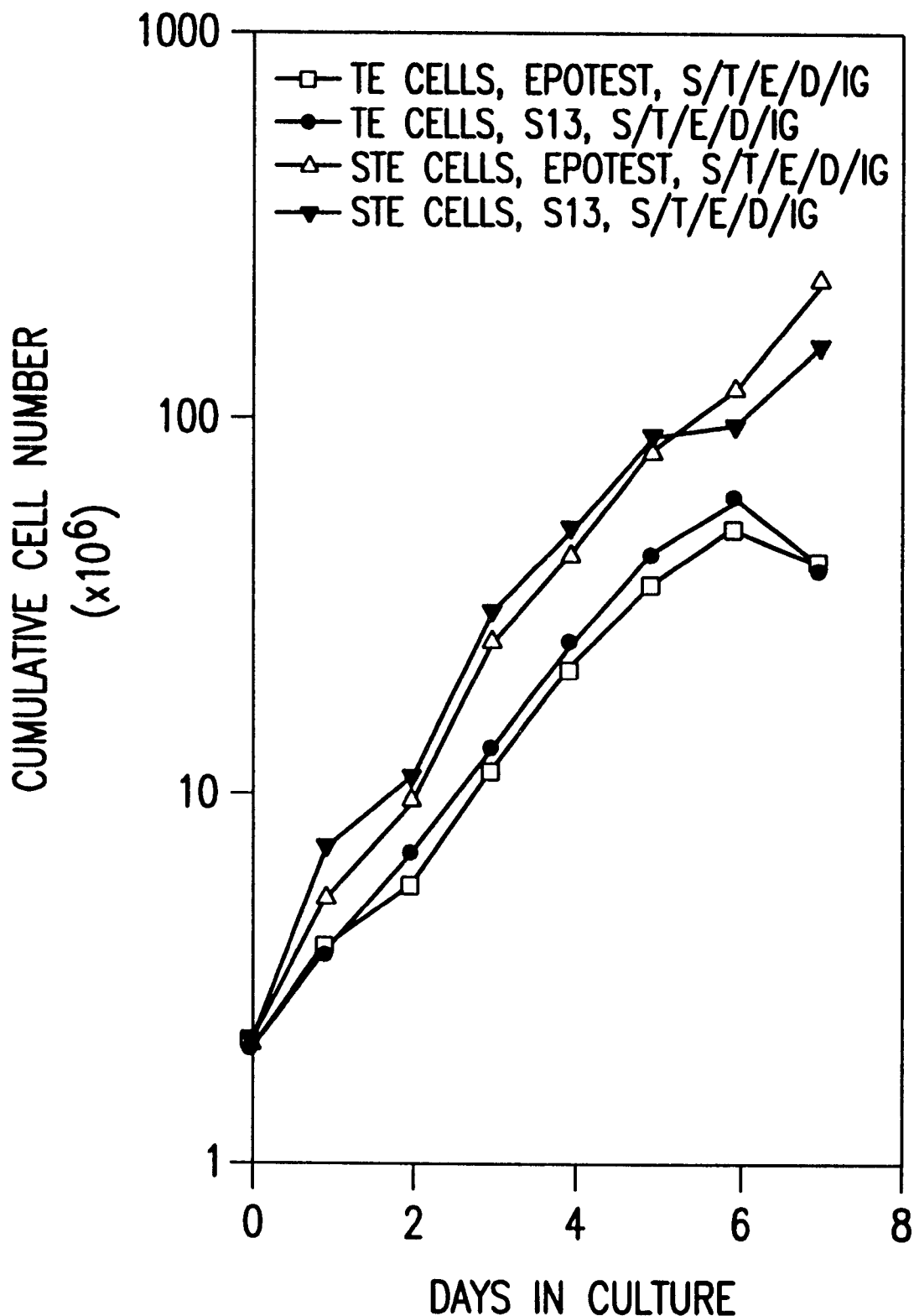
FIG. 9B: Definition of insulin-like growth factor (IGF-1) as one of the factors responsible for the activity in chicken serum

As a positive control, the SCF progenitors were treated during the 4-day induction period with SCF, TGFα and oestradiol (FIG. 9A, black triangles). After transfer into TE medium the cells grew out very much faster, as expected, and there was only a 5 day delay (lag-phase) in outgrowth. This corresponds to the results shown in Example 1 (FIG. 1, arrows).

A surprising result was obtained when the cells were treated with SCF, TGFα, oestradiol and dexamethasone during the induction period. Not only did the cells grow much faster during the induction period than in the controls, but also after transfer into TE medium there was no appreciable lag phase—the cells carried on growing at a constant speed (FIG. 9A, white squares). This result shows that the addition of dexamethasone brings about the conversion of virtually all SCF progenitors into SCF/TGFα progenitors. Additional investigations using phosphotyrosine blot (Western blot with phosphotyrosine antibodies) showed that these cells expressed the expected quantities of c-ErbB.

The effect of dexamethasone could also be observed in cells grown only in the presence of SCF. The addition of dexamethasone in the presence of SCF speeded up the outgrowth of SCF/TGFα progenitors more strongly than in the positive control (SCF, TGFα, oestradiol, FIG. 9A, cf. black and white triangles. As in Example 5, it was apparent that the cells required the oestradiol contained in small amounts in the sera, in addition to SCF and dexamethasone, since the addition of the oestradiol antagonist designated ICI 164384 (Schroeder et al., 1993) limited the outgrowth of the cells to the extent observed in the negative control (FIG. 9A, cf. white lozenges and black circles). In addition, the cells required small concentrations of a c-ErbB ligand (unknown, contained in chicken serum).

These results show i) that dexamethasone is necessary, in addition to TGFα and oestradiol, for the growth of SCF/TGFα progenitors capable of self-renewal and ii) that this hormone greater accelerates the conversion of SCF progenitors into SCF/TGFα progenitors.

b) Growth of SCF/TGFα progenitors: insulin-like growth factor I (IGF-1) together with SCF, TGFα, oestradiol and dexamethasone replaces the chicken serum which is absolutely essential for cell growth.

All previous experiments with normal erythroid chicken precursor cells capable of self-renewal were linked to the presence of tested batches of chicken serum; it has not yet been possible to define all the factors capable of replacing chicken serum. The results described in a), namely that dexamethasone permits the growth of these cells in chicken sera treated with activated charcoal, led to a series of attempts to replace the chicken serum with defined factors. The definition of these factors necessary for chicken cells forms the basis for any corresponding requirements of human cells.

Since a factor mixture of SCF, TGFα, oestradiol and dexamethasone was ideal for promoting the development as well as the growth of SCF/TGFα progenitors, this mixture was used in media with and without chicken sera. As possible other factors for replacing chicken serum, insulin-like growth factor (IGF-1) and avian IL-6 (Chicken Myelomonocytic Growth Factor, cMGF) were investigated. The experiments were carried out in medium with (FIG. 9B, S13 medium) and without chicken serum (FIG. 9B, Epotest).

Of the factors tested, only IGF-1 was effective. FIG. 9B shows that in the presence of SCF (S), TGFα (T), oestradiol (E), dexamethasone (D) and IGF-1 (IG), both 16 day old SCF/TGFα progenitor cells (FIG. 9B, black circles, white triangles) and 9 day old bone marrow cells cultivated in SCF/TGFα and oestradiol (FIG. 9B, black and white triangles) proliferated equally rapidly in media with chicken serum (black symbols) and without chicken serum (white symbols). The effect could be detected over a period of >7 days. In the absence of IGF-1 the cells stopped growing completely after 2 days. The same results (no cell growth) were obtained when IGF-1 was replaced by cMGF.

EXAMPLE 7

Cultivation of human erythroid cells resembling the chicken SCF and chicken SCF/TGFα progenitors
a) Provisional definition of conditions which make it possible for human erythroid progenitors to grow out of bone marrow or peripheral blood Experiments were carried out using human haematopoietic cells. The assumption underlying these experiments was that human erythroid progenitors have an in vitro lifespan similar to that of human fibroblasts (50 to 70 generations), and this constitutes the basis for detecting human erythroid progenitors capable of self-renewal.

Figure 10A:
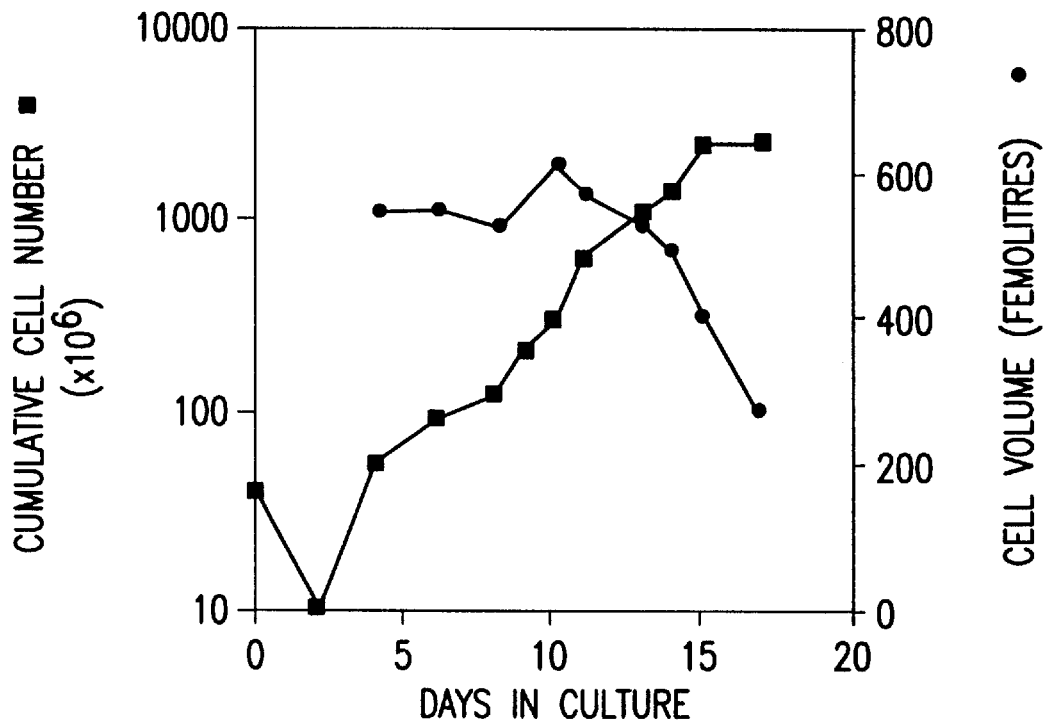
FIGS. 10A and 10B: Outgrowth of erythroid cells from human CD34+ cells from peripheral blood

Either bone marrow or peripheral blood from healthy donors served as the source for these experiments. From these sources, immature blood cells which express the CD34 cell surface antigen were concentrated using immune affinity chromatography as described by Shpall et al., 1994. The concentrated cells were seeded, as in the previous Examples, into a modified CFU-E medium (Hayman et al., 1993) containing human serum (Sigma) instead of chicken serum and iron-saturated human transferrin (Sigma) instead of conalbumin. The medium was supplemented with 20 ng TGFα (Promega), 20 ng recombinant EGF (Promega EGF was used in case the hypothetical member of the EGF receptor family present in erythroid cells does not have TGFα as a functional ligand), 100 ng of purified human SCF (Promega), $5 \times 10^{-7}$M oestradiol (in some experiments which served to characterise the cells other factors such as IL-3, IL-1 and LIF were added to the medium). The cell growth was monitored by cell counting and the cell types present in the cultures were analysed by cytocentrifugation on slides and histochemical staining on haemoglobin and histological dyes (Beug et al., 1982).
i) Experiments with bone marrow The initial attempts to grow erythroid progenitors from human bone marrow in modified CFU-E medium containing human serum, iron saturated human transferrin, 20 ng TGFα (Promega), 20 ng recombinant EGF (Promega), 100 ng of purified human SCF (Promega), 5 $\times 10^{-7}$M oestradiol and various other factors (10 ng each of IL-3, IL-6, IL-1 and LIF) per millilitre (ml), were initially unsuccessful. However, when recombinant EPO (3 International units/ml) was added to the medium, erythroid progenitors could be grown out, which remained immature for 13 days but which were substantially all differentiated on day 16. During this time the numbers of cells increased 25 to 50 fold; a more accurate measurement was impossible owing to the low cell numbers (only $2 \times 10^6$ of cells initially seeded out, therefore fewer than $10^5$ cells after 3–5 days). The proliferating cells obtained resembled human proerythroblasts, and surprisingly they were similar to the normal erythroid chicken progenitor cells (FIGS. 11A-1, 11A-2 and 11B, see below). During the first few days of the culture, and also after day 15, numerous nucleus-containing reticulocytes, nucleus-expelling cells and erythrocytes were visible, indicating that the differentiating reticulocytes in the culture normally differentiated to become erythrocytes and were also normally able to carry out the process of enucleation (ejection of the nucleus). Without EPO the cultures did not grow and contained very few immature erythroid cells. They contained mainly maturing monoblasts and various types of immature granulocytes (neutrophiles, eosinophiles, mast cells).

ii) Experiments with cells from peripheral blood The experiment described in i) was repeated with $40 \times 10^6$ CD34$^+$ cells, concentrated from human peripheral blood. $2 \times 10^6$ cells/ml in modified CFU-E medium plus SCF, TGFα and EGF, oestradiol and human recombinant EPO were seeded into tissue culture dishes and the cells were counted at the times specified, the average cell volumes being determined in an electronic cell counter of the CASY-1 type, Sharp system. Since the initial number of cells was greater than in the experiment carried out with bone marrow, the proliferation kinetics of the culture could be monitored accurately. FIG. 10A shows that the cell numbers decreased during the first 2 to 3 days, which can be put down to the maturation and/or cell death of partially differentiated progenitors. Subsequently, the cells proliferated exponentially with doubling times of between 20 and 30 hours up to day 15, after which no further growth was observed. The total increase in cell numbers during this growth phase was >300 fold. FIG. 10A also shows that during the phase of exponential growth the cells maintained their size (cell diameter between 9 and 10 μm, cell volumes between 500 and 600 femtolitres), which is a first indication that they remained immature.

Figure 10B:
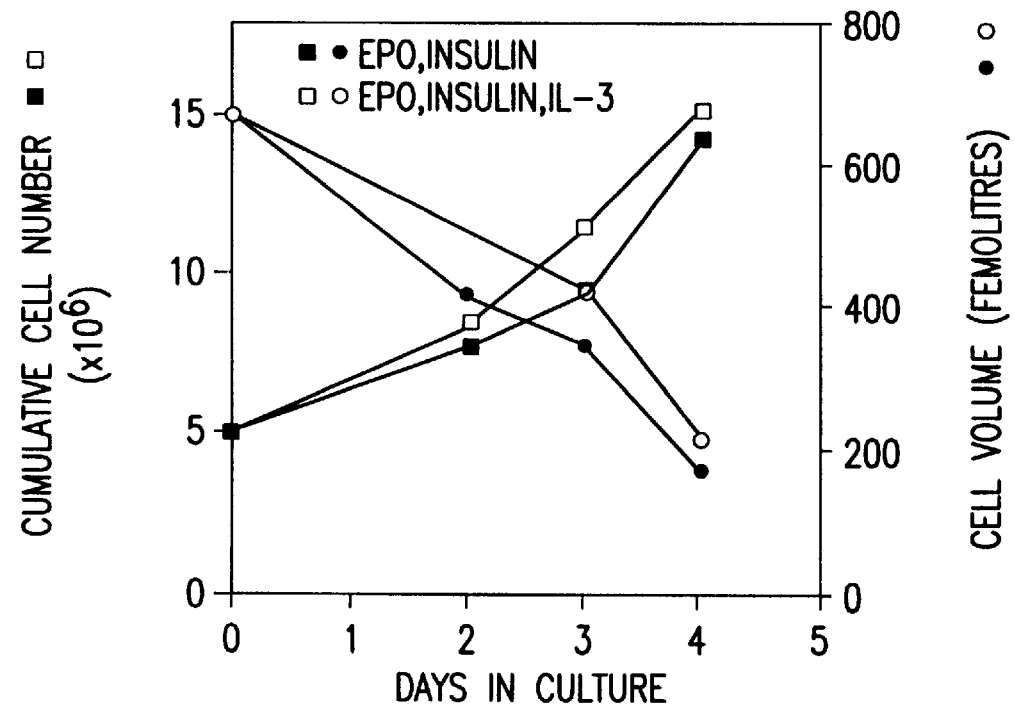

Since antigenic markers which distinguish human proerythroblasts from other myeloid or multipotent progenitors were not available for carrying out these experiments, and detection by histological staining is not truly definitive, indirect methods were used for determining the percentage of erythroid progenitors in the cultures: first, aliquots were stained at regular intervals of time using acid benzidine, which is a very sensitive haemoglobin detector (Graf and Beug, 1978). On the 6th day the cultures already contained 14% benzidine-positive cells and on days 10 and 11 these levels had risen to 51 and 63%. Since a pure culture of chicken SCF/TGFα progenitors contains between 30 and 60% benzidine-positive cells, these results indicate that on about day 10 the culture consisted predominantly of erythroid progenitors. This view could be confirmed by a test in which the cells were induced to differentiate: 1 aliquot of the 10 day old culture was washed and resuspended in modified CFU-E medium containing 10 units/ml of human recombinant EPO plus 10 ng/ml of insulin or IGF-1 (insulin like growth factor 1). A parallel aliquot was additionally given IL-3 (10 ng/ml). The data in FIG. 10B show that the cell numbers increased approximately 3-fold, whilst the cell volume decreased significantly at the same time, as is to be expected for differentiating erythroid cells. An acid benzidine staining carried out after 2 days yielded more than 95% benzidine-positive cells in the culture which had been given EPO/insulin alone. This indicates that the majority of the cells present before the induction of differentiation must have been erythroid, particularly as very few apoptotic cells were visible in the differentiating cultures after cytocentrifugation and histological staining (see below). The addition of IL-3 probably delayed differentiation; after 2 days, only 66% benzidine-positive cells were detected, and the cells grew somewhat faster, whilst their cell volume decreased more slowly (FIG. 10B).

b) Characterisation of the cells proliferating in SCF, TGFα, oestradiol and EPO

Figures 1, 2, 11A, 11B:
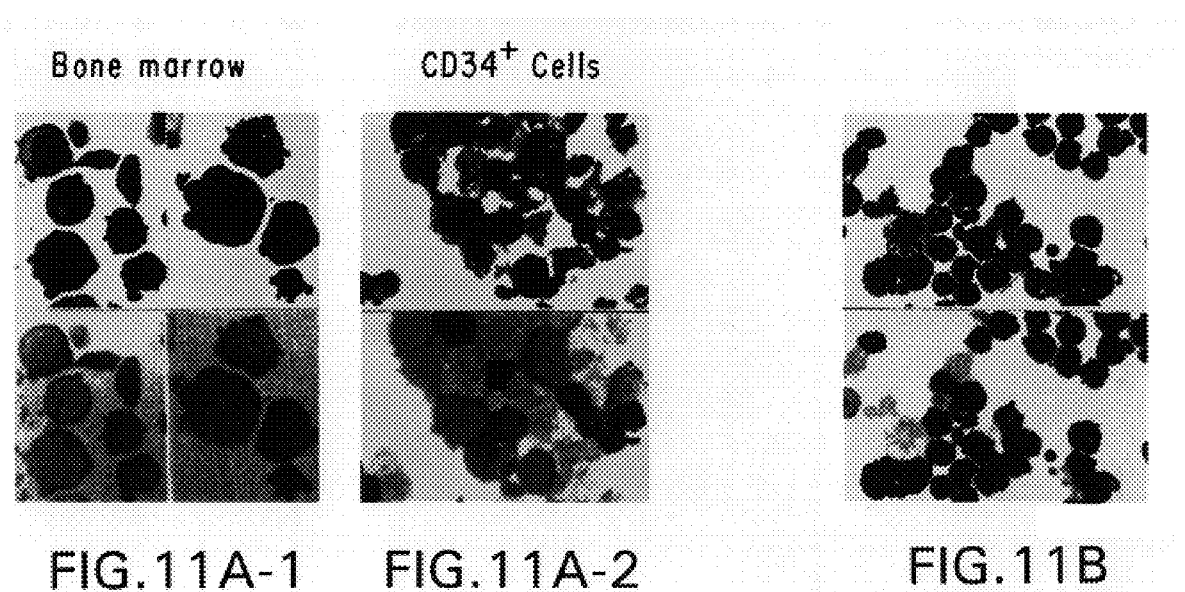

In order to determine whether the erythroid progenitors obtained by culture in SCF, TGFα plus EGF, oestradiol and recombinant EPO correspond to the chicken SCF/TGFα progenitors grown in the preceding Examples, the following two test methods were used:

Firstly, the cell types present in the cultures were characterised by centrifugation on slides and combined histological and histochemical staining for haemoglobin (Beug et al., 1992, see the stages defined therein). The intention was to determine how long immature haemoglobin-negative or slightly positive proerythroblasts would last in the cultures, so as to obtain some indication as to whether the erythroid progenitors actually underwent self-renewal, as was to be supposed on the basis of growth kinetics and size distribution (FIG. 10A). Proerythroblasts differ from other cells; in the staining used, by a central large cell nucleus, strongly basophilic cytoplasm, characteristic lapping of the cytoplasm seam and a slight staining with neutral benzidine which is distinguishable from myeloid cells. FIG. 11A, panel A (proliferating cells, bone marrow after 7 days, CD34$^+$ cells after 10 days) and FIG. 11B (differentiated after 10 days proliferation and 4 days differentiation) shows that a large percentage of the cells which last in the culture resemble benzidine-negative protoerythroblasts and in addition there was some myeloid cells. These results were obtained up till day 14, and then the percentage of maturing cells increased significantly. By contrast, the cells obtained after 4 days of differentiation induction (see above) constituted recticulocytes and, nucleus-expelling and mature erythrocytes (FIGS. 11A-1, 11A-2 and 11B), which is further confirmation that the cells kept in SCF, TGFα, oestradiol and EPO were actually prevented from entering into the differentiation induced by the above factors. FIG. 11A shows preparations of human bone marrow (BM) and CD34$^+$ cells (CD34), characterised by centrifugation on slides and combined histological and histochemical staining for haemoglobin, these preparations having been photographed under green light (above) and blue light (below) in order to pick up any histological details and haemoglobin staining. Er=erythrocytes and nucleus-expelling erythrocytes; R=reticulocytes; Pe=proerythroblasts; M=myeloid cells. FIG. 11B, panel B shows CD34$^+$ cells cultivated for 10 days, which were induced to differentiate for 4 days and photographed in a similar manner.

Figure 11C:
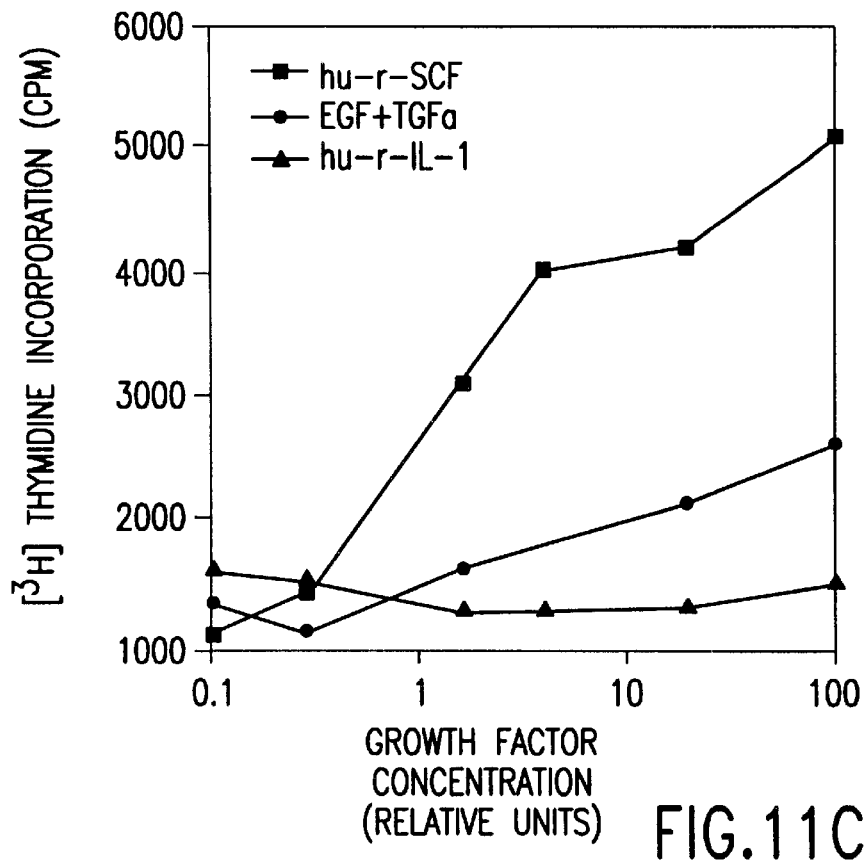
Figure 11D:
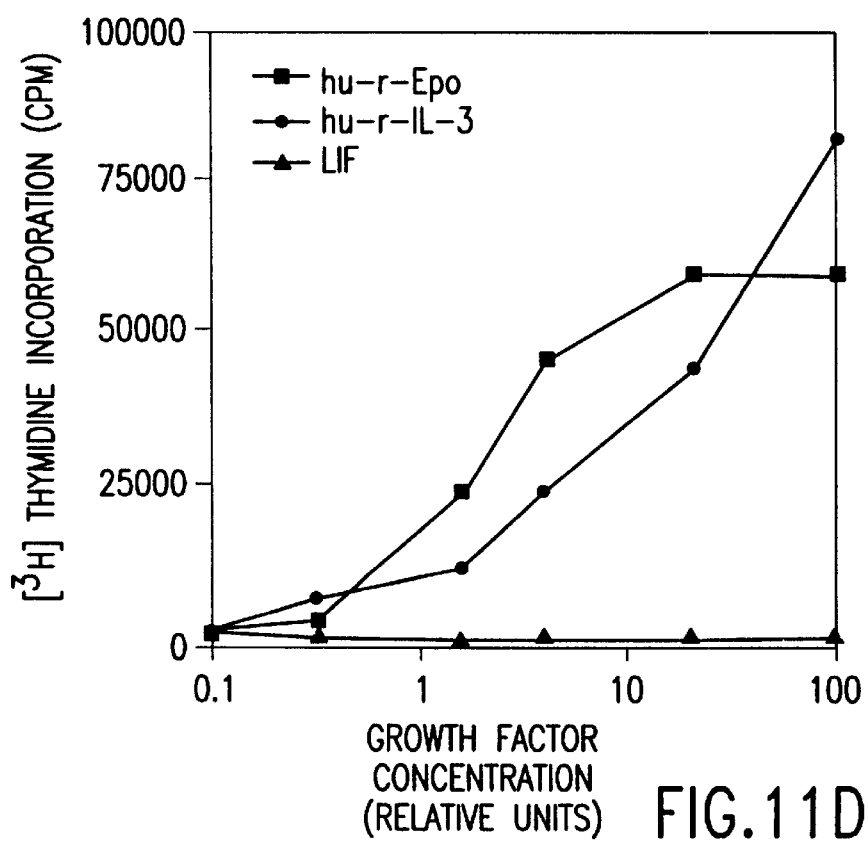

A clearer indication that cells resembling SCF/TGFα progenitors can actually be obtained from human erythroid progenitors was obtained by investigating whether the cells express both c-Kit and also a member of the c-ErbB/EGF receptor family and proliferate in response to the particular ligands. Since it was initially impossible to obtain any cultures which underwent self-renewal during the expected 50 to 70 divisions, it was thought that the majority of the cells in the cultures, particularly at early stages, correspond to SCF progenitors and that SCF/TGFα progenitors were only generated with low efficiency, presumably as a result of sub-optimal culture conditions. The reactivity of the human bone marrow cells to various growth factors was therefore tested using various growth factor assays (Leutz et al., 1984; Hayman et al., 1993). The results of these assays are shown in FIG. 11C (self-renewal factors TGFα/EGF, SCF) and FIG. 11D (differentiation factors (EPO, IL-3)). For these experiments,. CD34$^+$ cells were grown for 8 days, washed and tested for their growth factor dependency as described in Example 4, except that CFU-E medium was used without human serum. A relative growth factor concentration of 100 corresponded to 400 ng/ml of recombinant SCF, and 40 ng/ml each of TGFα or EGF; 10 ng/ml of human recombinant IL-1, 20 units/ml of human recombinant EPO, 40 ng/ml of human recombinant IL-3 and 10 ng/ml of recombinant murine LIF. The values shown are the averages from three measurements. The cells exhibited a strong reaction to SCF, and, more significantly, a weak but distinct reaction to a mixture of TGFα and EGF. On the other hand, there was no reaction to the two cytokines IL-1 and LIF, which act on very early, multi-potent haematopoietic cells. This leads one to conclude that the cells reacting to SCF are committed erythroid progenitors. As expected, the cells reacted just as strongly to the erythroid differentiation factors EPO and IL-3, again confirming that the culture predominantly contains erythroid cells.

EXAMPLE 8

Additional growth factors and steroid hormones induce self-renewal for long periods (>20 generations) in cultures of human proerythroblasts capable of terminal differentiation.

In Example 6, in the chicken system, results were obtained which were of potential significance for the outgrowth of human proerythroblasts capable of self-renewal:

1. Of the initially undefined factors in the chicken system which are necessary in addition to SCF, TGFα and oestradiol for the development of SCF progenitors into SCF/TGFα progenitors, two factors could be identified: the steroid hormone dexamethasone and the general growth factor insulin-like growth factor (IGF)-1.

2. The effect of dexamethasone on the self-renewal characteristics of human proerythroblasts was therefore investigated more thoroughly. Similarly, investigations were carried out to discover whether IGF-1, which makes the cells independent of chicken serum in the chicken system, shows at least growth-promoting properties on human cells. The results obtained were surprising: it was possible to increase the replication of human proerythroblasts during their in vitro lifespan from 200–1,000 fold to more than 100,000 fold. This allowed more accurate characterisation of the cell populations obtained by colony tests and FACS analysis. In addition, the differentiation characteristics of the proerythroblasts could be investigated much more accurately than in Example 7 because there were sufficient cells available.

a) Effect of dexamethasone

Figure 12A:
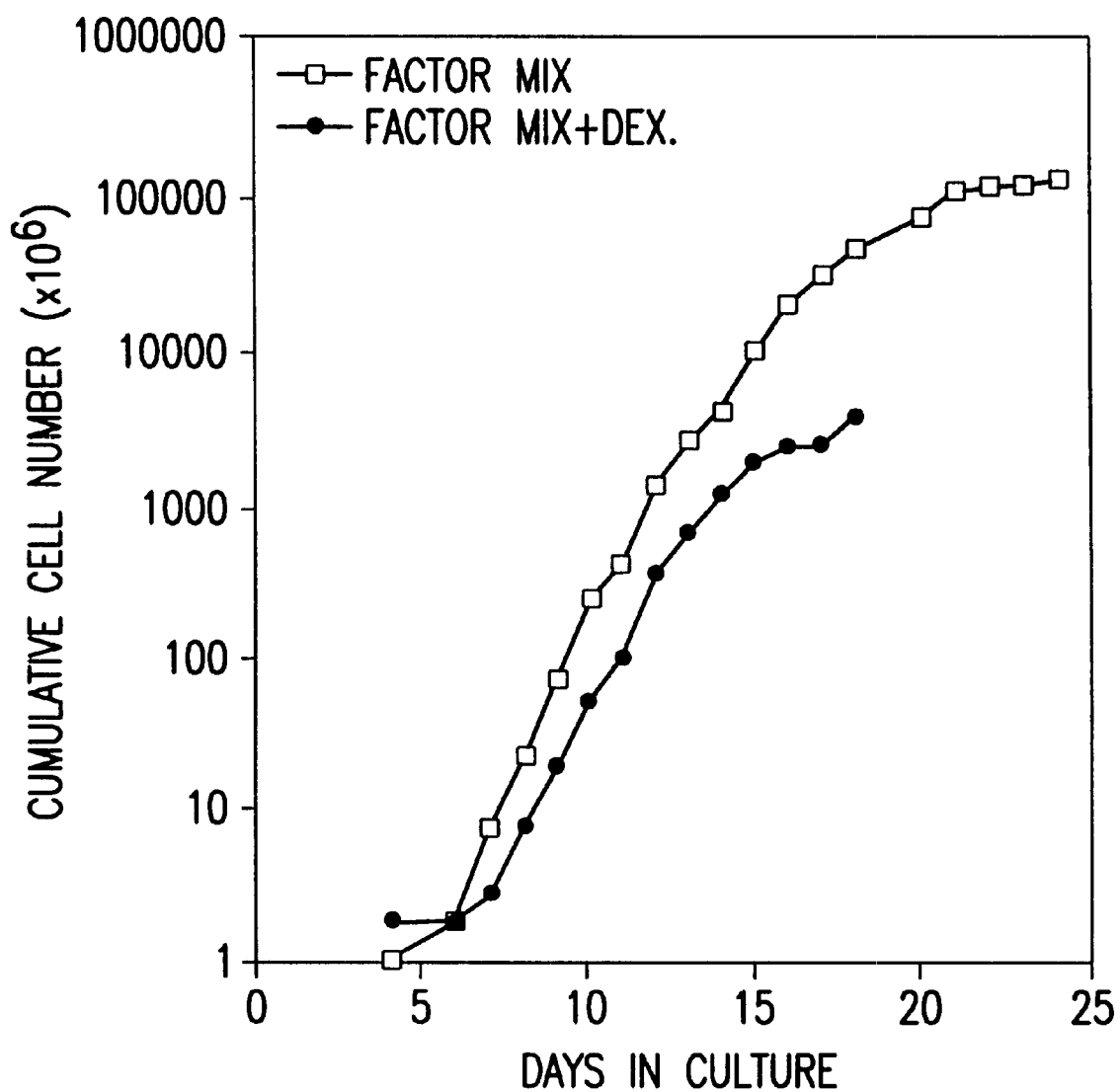
FIG. 12A: Prolonging the self-renewing potential of human CD34+ cells from umbilical cord blood by means of dexamethasone

Human CD34$^+$ cells from umbilical cord blood, purified as described in Example 7, part (ii)l w ere seeded into medium plus Epo, huSCF, TGFα and oestradiol, as described in Example 7. In addition to the above factors termed the "factor mix" $1 \times 10^6$M dexamethasone was added to a second culture. The cell growth was monitored until any detectable replication had ceased. The results are shown in FIG. 12A. As expected, cells grow exponentially in "factor mix" up till day 13/14 and showed a 1,000–2,000 fold cell multiplication (FIG. 12A, black circles). Unexpectedly, the parallel culture which was cultivated in factor mix plus dexamethasone proliferated exponentially until at least day 18 and thereafter its growth stopped only gradually (FIG. 12A, white squares), so as to obtain a 150,000 fold cell multiplication. If one assumes that some of the cells will always enter into spontaneous differentiation and hence only some of the immature cell population is available for maintaining the self-renewal potential of the culture, these data show that the proerythroblasts from human umbilical cord blood in the presence of EPO, SCF, TGFα, oestrogen and dexamethasone are capable of maintaining their self-renewal potential for at least 20 cell generations. This is substantially more than even the 7–10 cell divisions which human BFU-Es undergo within their normal development potential (Sawada et al., 1990). It is thus demonstrated i) that human erythroid progenitor cells, similarly to the corresponding cells in the chicken, can be induced to undergo a genuine change in their developmental potential, i.e. to sustained self-renewal, by combinations of tyrosine kinase ligands and ligands of steroid receptors.

b) Effect of IGF-1

Figure 12B:
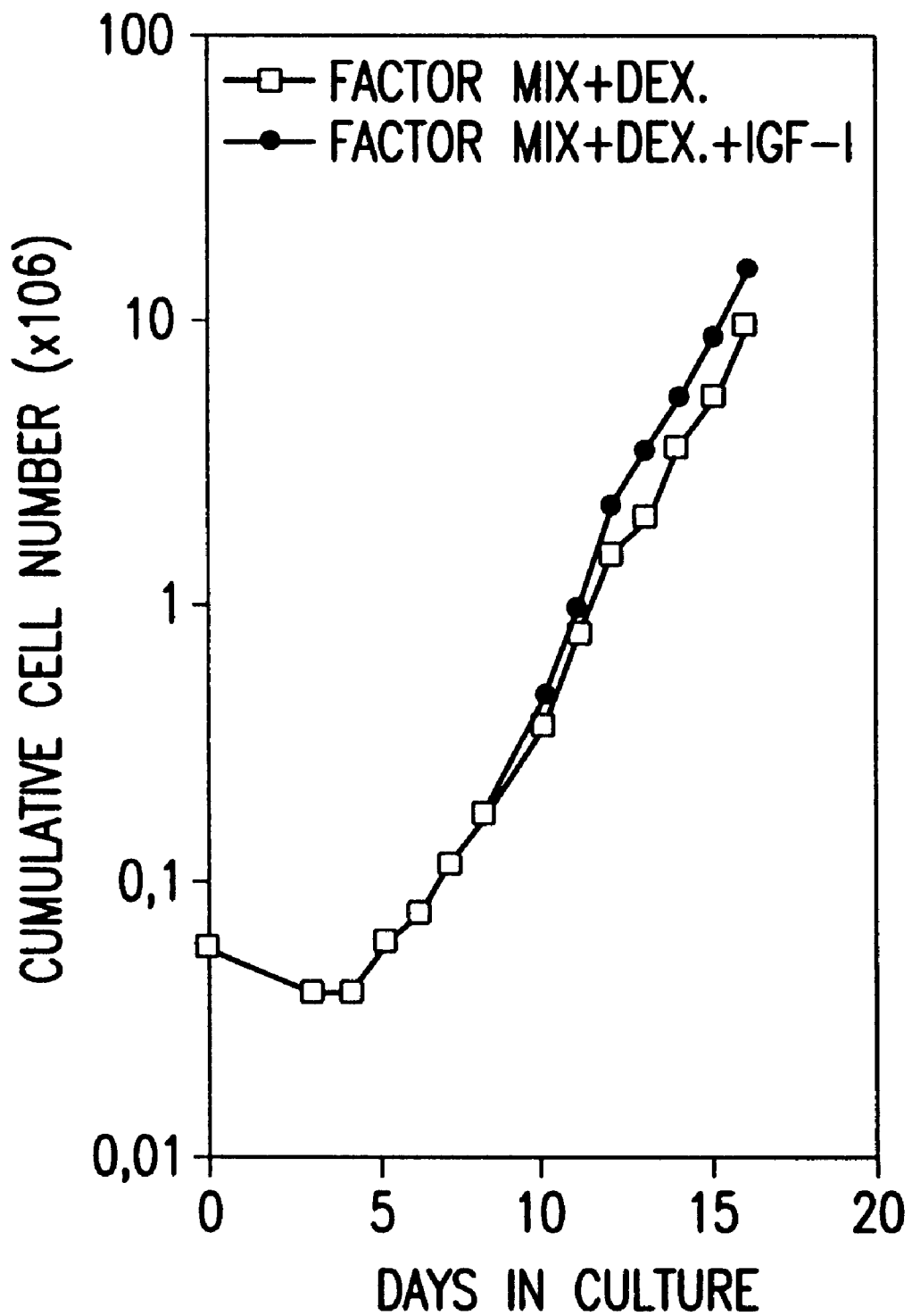
FIG. 12B: Increasing the growth of human cells from peripheral blood using IGF-1

CD34$^+$ cells from peripheral blood and an adult (obtained as in Example 7, part ii) were cultivated in "factor mix" plus dexamethasone until the cells began to grow exponentially. Then an additional 40 ng/ml of human recombinant IGF-1 (Promega) were added to one aliquot of the cells. As shown in FIG. 12B, the cells with IGF-1 (black circles) grew significantly faster than without this growth factor (white squares). Since the medium used contained 15% foetal calf serum and 4% serum from human umbilical cord blood (which can be expected to contain a basal concentration of IGF-1), an admittedly relatively small increase in the growth rate was achieved but it nevertheless shows that the cells react to IGF-1. This is also apparent from experiments in which the cells were cultivated overnight without factor, then stimulated for 5 and 10 minutes with IGF-1, lysed and investigated for receptor phosphorylation in the phosphotyrosine blot (see Example 2). The cells thus treated exhibited autophosphorylation of the intracellular 90 kD IGF-1 -receptor-chain and the 130 kD IRS-1 (insulin receptor substrate) protein, in the phosphotyrosine blot.

c) More accurate characterisation of the human erythroblasts capable of self-renewal, by means of colony tests and surface markers The surprising ability of the human proerythroblasts cultivated in "factor mix" with and without dexamethasone made it seem sensible to investigate these cells more closely for their developmental potential and their position within the erythroid developmental series. Two types of method were used for this:

Firstly, the cells were seeded into semi-liquid medium with suitable combinations of cytokines and 10 days later the type of colonies grown were counted. The following colony types were distinguished: i) burst forming unit erythroids (BFU-E), colonies consisting of 1,000 to >20,000 cells, which contain only erythrocytes and thus show that the starting cell is an immature progenitor which is committed to the erythroid lineage; ii) BFU mix, large colonies with >20,000 cells, which contain, apart from erythrocytes, cells of at least one other lineage and thus indicate multipotent starting cells; and iii) colony forming units granulocyte/macrophage (CFU-GM), colonies of 100 to >1,000 cells, which contain no erythrocytes, only myeloid cells (macrophages and/or granulocytes) and thus derive from non-erythroid progenitor cells.

Secondly, the cells were tested using suitable antibodies and FACS analysis for the expression of surface markers which are specific to cells of certain lineages and degrees of maturity. Although there are no surface markers in existence which when used individually will recognise exclusively human proerythroblasts, by combining a number of markers which are expressed on immature and/or mature erythroblasts with specific markers for myeloid cells (CD 33) and lymphoid cells (CD-3, CD-19) it is possible to determine with great certainty whether the cells belong to the erythroid lineage. The CD 71 (α-transferrin receptor) antibody is particularly suitable for this, as it admittedly stains all proliferating cells slightly but marks erythroid cells very strongly. Together with CD 117 (c-Kit, expressed only on totally immature, BFU-E-like erythroid cells and multipotent precursors and certain myeloid cells (mast cells)) and GPA (α-glycophorin, specific to partially mature erythroid cells), the CD-71 antibody makes it possible safely to determine proerythroblasts (CD 71 bright, CD 107 positive to slightly positive, GPA negative or slightly positive, CD33, CD3, CD 19 negative).

In order to test cells from the corresponding cultures for their membership of a lineage and their degree of maturity within the erythroid lineage, cell aliquots were taken from the cultures shown in FIG. 12A on day 13 and day 16 and subjected to the tests shown in Tables I to III. The cells taken from the culture without dexamethasone on day 16 were also separated according to density: in the chicken system, only cells with a density of <1.070 g/cm$^3$ are immature, cells with a density of >1,072 g/cm$^3$ are in all cases partially mature and required only 1–2 days to mature into erythrocytes, during which time they underwent only a few cell divisions. Corresponding fractions were prepared from the human cells and were tested separately for colony formation and surface markers.

The results are shown in Tables I to III. These show that the predominant type of colony is formed after both 13 and 16 days from BFU-Es, i.e. from immature erythroid progenitors. The effect of dexamethasone to keep the cells for longer in an immature state characterised by self-renewal is also made clear by the BFU-E numbers: the cultures with dexamethasone contain 2–2.5 times the number of immature colony-forming erythroid progenitors as without dexamethasone after both 13 and 16 days. The data also show that the cell population consists overwhelmingly of committed erythroid progenitors. After both 13 and 16 days, more than 90% of the colony-forming cells are purely erythroid progenitors and the proportion of multipotent (BFU-mix) and myeloid "committed" progenitors is only 3–6%. Interestingly, dexamethasone also stimulates the content of multipotent progenitors 3–6 fold, whereas the effect on the myeloid progenitors is much weaker.

As expected, the denser fraction (>1.072 g/cm$^3$) of 16 day old umbilical cord blood cells was incapable of forming colonies in semi-liquid methocel medium. Its more mature nature was also confirmed by marker analysis.

Tables II and III also show that the results of the marker analysis in the FACS fully confirmed the conclusions drawn from the colony tests. All the cultures contained only a small amount of myeloid cells (10–20% after 13 days, 5–7% after 16 days, no lymphoid cells and scarcely any CD34 positive cells (around 5%) data not show). Around 85% of the cells are strongly CD71 positive but only a few percent of the cells are GPA positive. The effect of dexamethasone of keeping the progenitor cells in an immature state is also clarified by the CD 107 (c-Kit) expression: on day 16 (when the culture without dexamethasone was clearly decreasing in speed of growth; see FIG. 12A) only 21% of the cells are c-Kit positive, whereas in the exponentially growing parallel culture kept in the presence of dexamethasone, more than 50% of the cells were c-Kit positive. The partially mature state of the denser fraction from the 16 day old culture was confirmed by marker analysis: only 53% of the cells were CD71 positive (maturing cells lose the transferrin receptor) whereas 66% of the cells were GPA positive.

To summarise, characterisation of the cultures from umbilical cord blood showed the following:

i) The cultures consisted predominantly of immature, proerythroblast-like progenitors which are committed to the erythroid lineage but can still form large erythroid colonies (BFU-E). Contamination with multipotent cells and cells of other lineages makes up less than 10%.

ii) The effect of dexamethasone, together with other factors, of -inducing the capacity of human proerythroblasts for sustained self-renewal (more than 16 cell divisions) is clearly reflected in analysis of the colonies and markers: both the capacity to form BFU-E (and BFU-E mix) and the capacity to express c-Kit are critically boosted by dexamethasone.

d) Regulation of the differentiation of in vitro cultivated proerythroblasts from umbilical cord blood: application of the results obtained in the chicken system.

Figure 13:
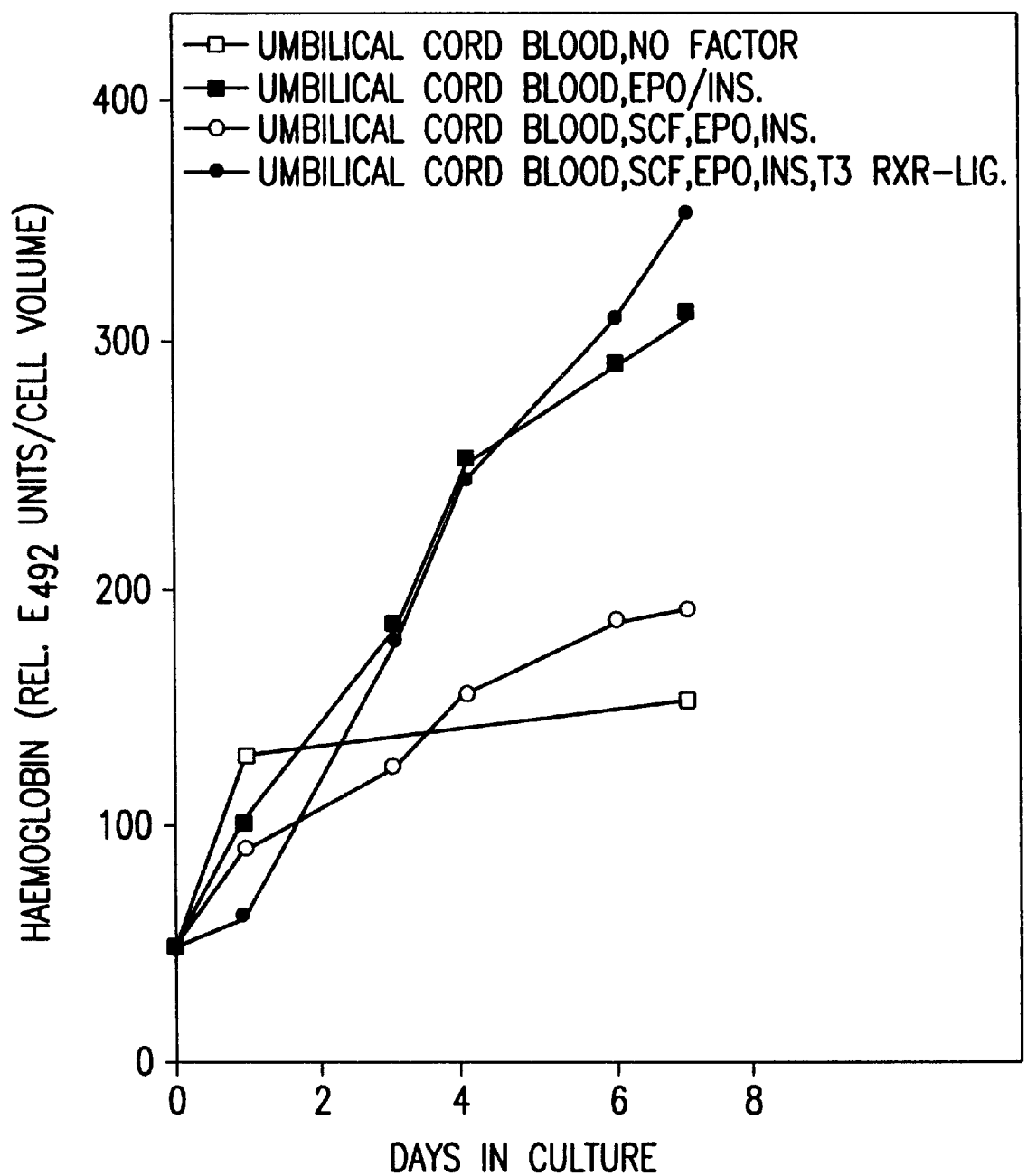
FIG. 13: Comparing the properties of outgrowing human erythroid progenitors with chicken cells In the Examples which follow, the materials and methods described by Hayman et al., 1993 were used unless otherwise stated. In Examples 1–6, chicken cells were used and in Examples 7 and 8 human cells were used.

A major advantage of normal erythroid progenitor cells capable of self-renewal in the chicken system was that after the removal of "self renewal factors" (SCF, TGFα and oestradiol) and replacement of these factors with differentiation factors (Epo, insulin) the cells differentiated out with normal kinetics and undergoing the expected number of cell divisions (Hayman et al., 1993). Example 7 has already shown that this observation could be applied in principle to human erythroblasts: human proerythroblasts cultivated in vitro matured in recombinant human Epo and insulin into enucleating (nucleus-expelling) erythrocytes (Example 7, FIGS. 10A and 10B). The presence of larger amounts of human proerythroblasts clearly capable of self-renewal made it possible to investigate this differentiation induction quantitatively. Moreover, it was now possible to analyse the effect of further factors on the differentiation programme of the cells. In the chicken system it was possible to show that SCF in the presence of Epo and insulin was able to significantly delay erythroid differentiation or virtually prevent it during the first 4–5 days (Hayman et al., 1993). Moreover, the thyroid hormone T3 (triodo-tyronine), particularly together with ligands of the co-receptor RXR, was capable of speeding up the erythroid differentiation and completely reversing the slowing down of the erythroid differentiation caused by SCF (Schroeder et al., 1992; Beug et al., 1994). It was therefore of interest to discover whether these observations made with regard to the chicken system were also valid for the human system. Whereas a significant effect of SCF, which might be interpreted as a delay in differentiation, on purified human BFU-E could be detected (Dai et al., 1991; Sawada et al., 1991) there are no known direct investigations into the effect of T3 on the development of purified erythroid progenitors. The experiments were carried out with 16 day old cells from the culture kept with "factor mix" and dexamethasone. The cells were centrifuged, washed in medium without factors and cultivated in a density of 1–2×10$^6$ cells/ml in the various differentiating media. The differentiating medium contains 2% human serum (from umbilical cord blood) and either no further additives (FIG. 13, white squares; no factor), 10 units/ml of human recombinant Epo plus 10 ng/ml of insulin (FIG. 13, Epo, Ins; black squares), Epo, Ins plus 100 ng of human SCF (FIG. 13, SCF, Epo, Ins; white circles) and the above factors plus 200 nm triiodothyronine and 10$^{-6}$M 9 cis retinolic acid (FIG. 13, SCF, Epo, Ins, T3, RXR Lig.; black circles). During the differentiation the cells were cultivated at a density of 2–4×10$^6$ cells/ml and fresh factors were added daily. At the times specified the cell volume was determined in an electronic cell counter of the type CASY-1, sharp system (see Example 7). At the same time, the haemoglobin content of cell aliquots of known cell number was determined by photometric measurement (Kowenz et al., 1987). The results are shown in FIG. 13. Whereas the haemoglobin content/cell volume scarcely increased in the absence of Epo/Ins (FIG. 13, white squares), in the presence of Epo/insulin there was a sharp (approximately 8 fold) increase in the haemoglobin content/cell volume (FIG. 13, black squares). Surprisingly, SCF delayed the erythroid differentiation induced by Epo/insulin just as in the chicken system (FIG. 13, white circles), whereas the addition of thyroid hormone (T3) plus RXR ligand completely reversed this delay in differentiation by SCF (FIG. 13, black circles), again exactly analogously to the data obtained in the chicken system.

To summarise, these data show that human proerythroblasts capable of self-renewal in culture mature, dependent on erythropoietin, in culture into mature erythrocytes which accumulate haemoglobin. This process is delayed by SCF and accelerated by T3 (as in purified human BFU-Es, Sawada et al., 1991).

TABLE I

| Cell type | Colony type (per 10$^5$ cells) | | |
| --- | --- | --- | --- |
| | BFU-E | BFU-mix | CFU-GM |
| 1 | 2250 | 60 | 70 |
| 2 | 5750 | 400 | 200 |
| 3 | 1200 | 45 | 115 |
| 4 | <1 | <1 | <1 |
| 5 | 2500 | 105 | 100 |
| 6 | ND | ND | ND |

ND = not detected
1: Umbilical cord blood (13 days, factor mix)
2: Umbilical cord blood (13 days, factor mix + dexamethasone)
3: Umbilical cord blood (16 days, factor mix, immature fraction <1.070 g/cm$^3$)
4: Umbilical cord blood (16 days, factor mix, mature fraction >1.072 g/cm$^3$)
5: Umbilical cord blood (16 days, factor mix + dexamethasone)
6: Peripheral blood (CD34$^+$, 9 days, factor mix + dexamethasone)

TABLE II

| | Cell surface marker | | |
| --- | --- | --- | --- |
| | immature | | |
| Cell type | CD71 (Transferrin receptor) | CD117 (c-Kit, SCF-receptor) | erythroid GPA (glycophorin) |
| 1 | ND | ND | 66% |
| 2 | ND | ND | 20% |
| 3 | 88% | 21% | 9% |
| 4 | 53% | 21% | 66% |

TABLE II-continued

| | Cell surface marker | | |
|---|---|---|---|
| | immature | | |
| Cell type | CD71 (Transferrin receptor) | CD117 (c-Kit, SCF-receptor) | erythroid GPA (glycophorin) |
| 5 | 84% | 51% | 7% |
| 6 | 80% | 65% | 30% |

ND = not detected
1: Umbilical cord blood (13 days, factor mix)
2: Umbilical cord blood (13 days, factor mix + dexamethasone)
3: Umbilical cord blood (16 days, factor mix, immature fraction <1.070 g/cm$^3$)
4: Umbilical cord blood (16 days, factor mix, mature fraction >1.072 g/cm$^3$)
5: Umbilical cord blood (16 days, factor mix + dexamethasone)
6: Peripheral blood (CD34$^+$, 9 days, factor mix + dexamethasone)

TABLE III

| | Cell surface marker | |
|---|---|---|
| Cell type | non-erythroid CD22 (gran.) | CD2, CD19 (B-cells, T-cells) |
| 1 | 10% | <0.1% |
| 2 | 20% | <0.1% |
| 3 | 5% | <0.1% |
| 4 | <0.1% | <0.1% |
| 5 | 7% | <0.1% |
| 6 | 5% | ND |

ND = not detected
gran. = granulocyte cells
1: Umbilical cord blood (13 days, factor mix)
2: Umbilical cord blood (13 days, factor mix + dexamethasone)
3: Umbilical cord blood (16 days, factor mix, immature fraction <1.070 g/cm$^3$)
4: Umbilical cord blood (16 days, factor mix, mature fraction >1.072 g/cm$^3$)
5: Umbilical cord blood (16 days, factor mix + dexamethasone)
6: Peripheral blood (CD34$^+$, 9 days, factor mix + dexamethasone)

LITERATURE

Beug, H., Palmieri, S., Freudenstein, C., Zentgraf, H. and Graf, T., 982. Cell 28, 907.

Beug, H., Döderlein, G. and Zenke, M., 1992, in Nuclear Processes and Oncogenes, (P. A. Sharp, ed.) p.53, Academic Press Inc., Harcourt Brace Jovanovich, Publishers San Diego.

Beug, H., Müllner, E. W., and Hayman, M. J., 1994. Curr. Op. Cell Biol. 6, 816–824.

Boulay, J. L. and Paul, W. E., 1993, Current Biology 3, 573–581

Dai, C. H., Krantz, S. B., and Zsebo, K. M., 1991. Blood 78, 2493–2497.

Daley, G. Q., Van Elten, R. A. and Baltimore, D., 1990, Science 247, 824–830.

Elefanty, A. G., Hariharan, I. K. and Cory, S., 1990, EMBO J. 9, 1069–1078.

Fantl, W. J. et al., 1993, Annual Reviews of Biochemistry 62, 453–481.

Galimi, F., Bagnara, G. P., Bonsi, L., Cottone, E., Follenzi, A., Simeone, A. and Comoglio, P. M., 1994, J. Cell. Biol. 127, 1743–1754.

Graf, T. and Beug, H., 1978, Biochim. Biophys. Acta 516, 269–299.

Hayman, M. J., Meyer, S., Martin, F., Steinlein, P. and Beug, H., 1993, Cell 74, 157–169.

Hogan, B., 1993, Current Biology 170–172.

Jolly, D., 1994, Cancer Gene Therapy 1, 51.

Kaipainen, A., Korhonen, J., Pajusola, K., Aprelikova, O., Persico, M. G., Terman, B. I. and Alitalo, K., 1993, J. Exp. Med. 178, 2077–2088.

Keller, G., 1992, Curr. Opinion in Immunology 4, 133–139.

Kelliher, M. A., McLaughlin, J., Witte, O. N. and Rosenberg, N., 1990, Proc. Natl. Acad. Sci. USA 87, 6649–6653.

Kowenz, E., Leutz, A., Doderlein, G., Graf, T., and Beug, H., 1987. In Modern Trends in Human Leukemia VII, R. Neth, R. C. Gallo, M. F. Greaves and H. Kabisch,.eds. (Heidelberg: Springer Verlag), pp. 199–209.

Laufer, E., 1993, Current Biology 3, 306–308.

Lax, I., Johnson, A., Howk, R., Sap, J., Bellot, F., Winkler, M., Ullrich, A., Vennström, B., Schlessinger, J. and Givol, D., 1988, Mol. Cell. Biol. 8, 1970–1978.

Leutz, A., Beug, H. and Graf, T., 1984, EMBO J. 3, 3191–3197.

Metclaf, D., 1980, Proc.Natl.Acad.Sci. USA 77, 5327–5330.

Mitani, K. and Caskey, C. T., 1993, Trends in Biotechnology 11, 162–166.

Peles, E. and Yarden, Y., 1993, Bioessays 15, 815–824.

Rolink, A., Kudo, A., Karasyama, H. and Kikuchi, Y., 1991, EMBO J. 10, 327–336.

Sawada, K., Krantz, S. B., Dai, C. H., Koury, S. T., Horn, 9. T., Glick, A. D., and Civin, C. I., 1990. J. Cell. Physiol. 142, 219–230.

Sawada, K., Krantz, S. B., Dai, C. H., Sato, N., Ieko, M., Sakurama, S., Yasukouchi, T., and Nakagawa, S., 1991. J. Cell. OPhysiol. 149, 1–8.

Sawada K., et al., J. Cell. Physiol. 142, 219–230

Sawyers, C. L., Denny, C. T. and Witte, O. N., 1991, Cell 64, 337–350.

Schroeder, C., Gibson, L., Zenke, M. and Beug, H., 1992, Oncogene 7, 217–227.

Schroeder, C., Gibson, L., Nordström, Ch. and Beug, H., 1993, EMBO J. 12, 951–960.

Shpall, E. J. Jones, R. B., Bearman, S. I., Franklin, W. A., Archer, P. G., Curiel, T., Bitter, M. Claman, H. N. Stemmer, S. M., Purdy, M., Myers, S. E., Hami, L., Taffs, S., Heimfeld, S., Hallagan, J., Berenson, R. J., 1994, J. Clin. Oncol. 12, 28–36.

Tamagnone, L., Partanen, J., Armstrong, E., Lasota, J., Ohgami, K., Tazunoki, T., LaForgia, S., Huebner, K. and Alitalo, K., 1993, Oncogene 8, 2009–2014.

Tepper, R. I. and Mule, J. J., 1994, Human Gene Therapy 5, 153.

Till, J. E. and McCulloch, M., 1980, Biochim. Biophys. Acta 605, 431–459.

Van der Geer, P., Hunter, T. and Lindberg, R. A., 1994, Annual Review Cell Biol. 10, 251–337.

Vile, R. and Russel S., 1994, Gene Therapy 1, 88.

Zatloukal, K., Schmidt, W., Cotten, M., Wagner, E., Stingl. G. and Birnstiel, M. L., 1993, Gene 135, 199.

Hematopoietic Stem Cells, The Mulhouse Manual, 1994, Hsg. Wunder, E., Sovalet, H., Henon, P. R. and Serke, S.

We claim:

1. A process for in vitro expansion of non-immortalized hematopoietic CD34$^+$ progenitor cells of erythroid lineage without simultaneous differentiation, comprising
   (a) growing erythroid CD34$^+$ progenitor cells in a medium suitable for erythroid cell growth; and
   (b) exposing said cells to a combination of growth factors comprising
      (i) at least one estrogen receptor ligand;
      (ii) at least one glucocorticoid receptor ligand; and
      (iii) at least one tyrosine kinase receptor ligand;
for a time sufficient to induce said progenitor cells to begin self-renewal and thereby expansion, without simultaneous differentiation.

2. The process of claim 1, wherein subsequent to step (b), said cells are exposed to at least one factor required for sustained self-renewal.

3. The process of claim 2, wherein said CD34$^+$ progenitor cells are human cells.

4. The process of claim 3, wherein said erythroid CD34$^+$ progenitor cells are bone marrow cells, peripheral blood cells, or umbilical cord blood cells.

5. The process of claim 1, wherein at least two tyrosine kinase receptor ligands are employed in step (b).

6. The process of claim 5, wherein said two tyrosine kinase receptor ligands bind to different classes of tyrosine kinase receptors.

7. The process of claim 6, wherein said different classes of kinase receptors differ with respect to their kinase domain.

8. The process of claim 7, wherein one tyrosine kinase receptor ligand binds to a tyrosine kinase receptor selected from the sub-class of tyrosine kinase receptors having an uninterrupted tyrosine kinase domain, and a second tyrosine kinase receptor ligand binds to a tyrosine kinase receptor selected from the sub-class of tyrosine kinase receptors having a kinase insertion sequence.

9. The process of claim 5, wherein said combination of growth factors comprises
   (i) a ligand of c-Kit; and
   (ii) at least one ligand of a receptor selected from the group consisting of the epidermal growth factor family of receptors and the hepatocyte growth factor family of receptors.

10. The process of claim 5, wherein said combination of growth factors comprises:
    (i) stem cell factor;
    (ii) estradiol;
    (iii) at least one of dexamethasone and hydrocortisone; and
    (iv) at least one of transforming growth factor α, epidermal growth factor and hepatocyte growth factor.

11. The process of claim 5, wherein in step (b), said combination of growth factors further comprises at least one other factor capable of accelerating the initiation of self-renewal of said cells, and wherein said other factor is a cytokine, a ligand of a tyrosine kinase receptor, or a ligand of a serine kinase receptor.

12. The process of claim 11, wherein said other factor is erythropoietin.

13. The process of claim 11, wherein said other factor is insulin-like growth factor 1.

14. The process of claim 11, wherein said combination of growth factors comprises stem cell factor, dexamethasone, estradiol, erythropoietin, insulin-like growth factor 1, and at least one of transforming growth factor α, epidermal growth factor and hepatocyte growth factor.

15. The process of claim 11, wherein subsequent to step (b), said cells are exposed to at least one factor required for sustained self-renewal.

16. The process of claim 15, wherein said factor required for sustained self-renewal is selected from the group consisting of a ligand of the family of epidermal growth factor receptors, a ligand of the family of hepatocyte growth factor receptors, stem cell factor, erythropoietin, and insulin-like growth factor 1.

17. The process of claim 15, wherein said factor required for sustained self-renewal is selected from the group consisting of transforming growth factor α, epidermal growth factor, and hepatocyte growth factor.

* * * * *